US006869949B2

(12) United States Patent
Senn-Bilfinger et al.

(10) Patent No.: US 6,869,949 B2
(45) Date of Patent: Mar. 22, 2005

(54) POLYSUBSTITUTED IMIDAZOPYRIDINES AS GASTRIC SECRETION INHIBITORS

(75) Inventors: Jörg Senn-Bilfinger, Constance (DE); Wilm Buhr, Constance (DE); Peter Zimmermann, Constance (DE); Bernhard Kohl, Constance (DE)

(73) Assignee: Altana Pharma AG, Constance (DE)

( * ) Notice: Subject to any disclaimer, the term of this patent is extended or adjusted under 35 U.S.C. 154(b) by 77 days.

(21) Appl. No.: 10/380,624

(22) PCT Filed: Oct. 23, 2001

(86) PCT No.: PCT/EP01/12207

§ 371 (c)(1),
(2), (4) Date: Jul. 2, 2003

(87) PCT Pub. No.: WO02/34749

PCT Pub. Date: May 2, 2002

(65) Prior Publication Data

US 2004/0106642 A1 Jun. 3, 2004

(30) Foreign Application Priority Data

Oct. 25, 2000 (EP) .............................................. 001231331

(51) Int. Cl.[7] .................. A61K 31/4375; C07D 471/14; C07D 491/147

(52) U.S. Cl. .................... 514/233.2; 514/256; 514/293; 544/126; 544/333; 546/82; 546/83

(58) Field of Search ............................... 544/126, 333; 546/82, 83; 514/233.2, 256, 293

(56) References Cited

U.S. PATENT DOCUMENTS

| | | | |
|---|---|---|---|
| 4,468,400 A | | 8/1984 | Gold et al. ................. 514/292 |
| 6,160,119 A | * | 12/2000 | Senn-Bilfinger ............. 546/83 |
| 6,197,783 B1 | * | 3/2001 | Senn-Bilfinger et al. .... 514/293 |
| 6,384,048 B1 | * | 5/2002 | Senn-Bilfinger ............ 514/293 |
| 6,436,953 B1 | * | 8/2002 | Senn-Bilfinger ............ 514/293 |
| 6,503,923 B1 | * | 1/2003 | Senn-Bilfinger ............ 514/293 |

FOREIGN PATENT DOCUMENTS

| | | |
|---|---|---|
| WO | WO 95/27714 | 10/1995 |
| WO | WO 98/42707 | 10/1998 |
| WO | WO 98/54188 | 12/1998 |
| WO | WO 00/17200 | 3/2000 |
| WO | WO 00/26217 | 5/2000 |
| WO | WO 00/63211 | 10/2000 |
| WO | WO 01/72754 | 10/2001 |
| WO | WO 01/72755 | 10/2001 |
| WO | WO 01/72756 | 10/2001 |
| WO | WO 01/72757 | 10/2001 |

OTHER PUBLICATIONS

Senn–Bilfinger, J., et al., "Preparation of imidazonaphthyridines for prevention and treatment of gastrointestinal disease". Chemical Abstracts, vol. 132, No. 11, Abstract No. 137385, 2000.

Kaminksi, James J., et al., "Antiulcer Agents. 4. Conformational Considerations and the Antiulcer Activity of Substituted Imidazo{[1,2–a ] pyridines and Related Analogues". J. Med. Chem.: 32, 1686–1700, 1989.

Kaminski, James J., et al., "Antiulcer Agents. 5. Inhibition of Gastric H+/K+–ATPase by Substituted Imidazo[1,2–a] pyridines and Related Analogues and Its Implication in Modeling the High Affinity Potassium Ion Binding Site of the Gastric Proton Pump Enzyme". J. Med. Chem.: 34, 533–541, 1991.

Kaminski, James J., et al., "Antiulcer Agents. 6. Analysis of the in Vitro Biochemical and in Vivo Gastric Antisecretory Activity of Substituted Imidazo{[1,2–a ] pyridines and Related Analogues Using Comparative Molecular Field Analysis and Hypothetical Active Lattice Methodologies". J. Med. Chem.: 40, 427–436, 1997.

* cited by examiner

*Primary Examiner*—Fiona T. Powers
(74) *Attorney, Agent, or Firm*—Nath & Associates PLLC; Todd L. Juneau; Sheldon M. McGee

(57) ABSTRACT

The invention relates to imidazopyridines of a certain formula 1, in which the substituents and symbols have the meanings indicated in the description. The compounds have gastric secretion-inhibiting properties.

27 Claims, No Drawings

POLYSUBSTITUTED IMIDAZOPYRIDINES AS GASTRIC SECRETION INHIBITORS

TECHNICAL FIELD

The invention relates to novel compounds, which are used in the pharmaceutical industry as active compounds for the production of medicaments.

PRIOR ART

U.S. Pat. No. 4,468,400 describes triyclic imidazo[1,2-a] pyridines having various ring systems fused to the imidazopyridine parent structure, which should be suitable for the treatment of peptic ulcers. In international patent applications WO98/42707, WO98/54188, WO00/17200 and WO00/26217, as well as in international patent applications WO00/63211, WO01/72756, WO01/72754, WO01/72755 and WO01/72757, tricyclic imidazopyridine derivatives having a very specific substitution pattern are disclosed, which should likewise be suitable for the treatment of gastric and intestinal diseases.

SUMMARY OF THE INVENTION

The invention relates to compounds of the formula 1

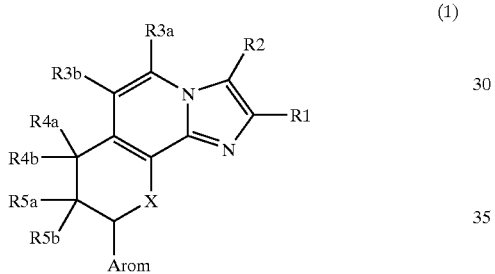

(1)

in which
- R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
- R2 is hydrogen, 1–4C-alkyl, aryl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
- R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
- R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
  where
  - R31 is hydrogen, 1–7C-alkyl, hydroxy-1–4C-alkyl or 1–4C-alkoxy-14C-alkyl and
  - R32 is hydrogen, 1–7C-alkyl, hydroxy-1–4C-alkyl or 1–4C-alkoxy-1–4C-alkyl,
  or where
  - R31 and R32 together, including the nitrogen atom to which both are bonded, are a pyrrolidino, piperidino or morpholino radical,
- one of the substituents R4a and R4b is hydrogen, 1–7C-alkyl, 2–7C-alkenyl, phenyl or phen-1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy, 1–4C-alkoxy-1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R41 or the radical R42, or in which R4a and R4b together are O (oxygen) or are 1–7C-alkylidene,
  where
  - R41 is a radical from which a hydroxy group is formed under physiological conditions,
  and where
  - R42 is —O—(CH$_2$)$_m$—S(O)$_n$—R6, —S(O)$_n$—(CH$_2$)$_m$—OH, —S(O)$_n$—(CH$_2$)$_m$—O—R6, —S(O)$_n$—(CH$_2$)$_m$—S(O)$_p$—R6, —O-Alk1-S(O)$_n$—R6, —S(O)$_n$—R6, —S(O)$_n$-Alk1-OH, —S(O)$_n$-Alk1-O—R6 or —S(O)$_n$-Alk1-S(O)$_p$—R6,
    in which
    - R6 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro,
    - Alk1 is substituted 2–7C-alkylene or 3–4C-alkenylene by 1–4C-alkyl, hydroxyl, oxo, carboxyl, halogen, amino, 1–4C-alkoxycarbonylamino or phenyl,
    - m is an integer from 2 to 7,
    - n is the number 0, 1 or 2 and
    - p is the number 0, 1 or 2,
- one of the substituents R5a and R5b is hydrogen, 1–7C-alkyl, 2–7C-alkenyl, phenyl or phen-1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy, 1–4C-alkoxy-1–4C-alkoxy-1–4C-alkoxy, 3–7G-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R51 or the radical R52, or in which R5a and R5b together are O (oxygen) or are 1–7C-alkylidene,
  where
  - R51 is a radical from which a hydroxy group is formed under physiological conditions,
  and where
  - R52 is —O—(CH$_2$)$_q$—S(O)$_r$—R7, —S(O)$_r$—(CH$_2$)$_q$—OH, —S(O)$_r$—(CH$_2$)$_q$—O—R7, —S(O)$_r$—(CH$_2$)$_q$—S(O)$_t$—R7, —O-Alk2-S(O)$_r$—R7, —S(O)$_r$—R7, —S(O)$_r$-Alk2-OH, —S(O)$_r$-Alk2-O—R7 or —S(O)$_r$-Alk2-S(O)$_t$—R7,
    in which
    - R7 is 1–7C-alkyl, halo-1–4C-alkyl, hydroxy-1–4C-alkyl, 1–4C-alkoxy-1–4C-alkyl, carboxy-1–4C- alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, Alk2 is 2–7C-alkylene or 3–4C-alkenylene substituted by 1–4C-alkyl, hydroxyl, oxo, carboxyl, halogen, amino, 1–4C-alkoxycarbonylamino or phenyl, q is an integer from 2 to 7,
r is the number 0, 1 or 2 and
t is the number 0, 1 or 2, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, which if desired, is wholly or partially halogen-substituted, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), triazolyl, isoxazolyl, pyridinyl, pyrimidinyl, quinolinyl and isoquinolinyl, where R8 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl, R9 is hydrogen, 1–4C-alkyl, 1–4C-alkoxy, 1–4C-alkoxycarbonyl, halogen, trifluoromethyl or hydroxyl, R10 is hydrogen, 1–4C-alkyl or halogen and
R11 is hydrogen, 1–4C-alkyl or halogen,
where
Aryl is phenyl or substituted phenyl having one, two or three identical or different substituents from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano, X is O (oxygen) or NH,
and their salts,
with the exclusion of those compounds claimed in international patent applications WO98/42707, WO98/54188, WO00/17200, WO00/26217, WO00/63211, WO01/72756, WO01/72754, WO01/72755 and WO01/72757.

DETAILED DESCRIPTION OF THE INVENTION

More particularly the invention relates to compounds of the formula 1

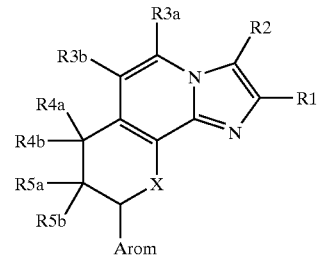

(1)

in which

R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl, R2 is hydrogen, 1–4C-alkyl, aryl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl, R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen, 1–7C-alkyl, 2–7C-alkenyl, phenyl or phen-1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4G-alkoxy-1–4C-alkoxy, 1–4C-alkoxy-1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R41 or the radical R42, or in which R4a and R4b together are O (oxygen) or are 1–7C-alkylidene, where R41 is a radical from which a hydroxy group is formed under physiological conditions, and where R42 is —O—(CH$_2$)$_m$—S(O)$_n$—R6, —S(O)$_n$—(CH$_2$)$_m$—OH, —S(O)$_n$—(CH$_2$)$_m$—O—R6, —S(O)$_n$—(CH$_2$)$_m$—S(O)$_p$—R6, —O-Alk1-S(O)$_n$—R6, —S(O)$_n$—R6, —S(O)$_n$-Alk1-OH, —S(O)$_n$-Alk1-O—R6 or —S(O)$_n$-Alk1-S(O)$_p$—R6, in which R6 is 1–7C-alkyl, halo-1–4C-alkyl, hydroxy-1–4C-alkyl, 1–4C-alkoxy-1–4C-alkyl, carboxyl-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, Alk1 is substituted 2–7C-alkylene or 3–4C-alkenylene by 1–4C-alkyl, hydroxyl, oxo, carboxyl, halogen, amino, 1–4C-alkoxycarbonylamino or phenyl, m is an integer from 2 to 7, n is the number 0, 1 or 2 and p is the number 0, 1 or 2, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy, 1–4C-alkoxy-1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R51 or the radical R52, or in which R5a and R5b together are O (oxygen) or are 1–7C-alkylidene, where R51 is a radical from which a hydroxy group is formed under physiological conditions, and where R52 is —O—(CH₂)$_q$—S(O)$_t$—R7, —S(O)$_r$—(CH₂)$_q$—OH, —S(O)$_r$—(CH₂)$_q$—O—R7, —S(O)$_r$—(CH₂)$_q$—S(O)$_t$—R7, —O-Alk2-S(O)$_r$—R7, —S(O)$_r$—R7, —S(O)$_r$-Alk2-OH, —S(O)$_r$-Alk2-O—R7 or —S(O)$_r$-Alk2-S(O)$_t$—R7, in which R7 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, Alk2 is 2–7C-alkylene or 3–4C-alkenylene substituted by 1–4C-alkyl, hydroxyl, oxo, carboxyl, halogen, amino, 1–4C-alkoxycarbonylamino or phenyl, q is an integer from 2 to 7, r is the number 0, 1 or 2 and t is the number 0, 1 or 2, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, which it desired, is wholly or partially halogen-substituted, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R8 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl, R9 is hydrogen, 1–4C-alkyl, 1–4C-alkoxy, 1–4C-alkoxycarbonyl, halogen, trifluoromethyl or hydroxyl, R10 is hydrogen, 1–4C-alkyl or halogen and R11 is hydrogen, 1–4C-alkyl or halogen, where Aryl is phenyl or substituted phenyl having one, two or three identical or different substituents from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano, X is O (oxygen) or NH, and their salts, where the following are excluded (a) compounds of the formula 1, in which R1 is 1–4C-alkyl, R2 is 1–4C-alkyl or hydroxy-1–4C-alkyl, R3a is hydrogen or halogen, R3b is hydrogen or halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, Arom is phenyl substituted by R8, R9, R10 and R11, where R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino, R9 is hydrogen, 1–4C-alkyl, 1–4C-alkoxy or halogen, R10 is hydrogen and R11 is hydrogen, X is O (oxygen) or NH, and their salts, (b) compounds of the formula 1, in which R1 is 1–4C-alkyl, R2 is 1–4C-alkyl or hydroxy-1–4C-alkyl, R3a is hydrogen or halogen,
R3b is hydrogen or halogen,
one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen),
where
R42 has the meanings indicated above,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen),
where
R52 has the meanings indicated above,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R1 is hydrogen,
X is NH,
and their salts,
(c) compounds of the formula 1, in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen, halogen, fluoro-1–4C-alkyl, 1–4C-alkyl, 2–4C-alkenyl or 2–4C-alkynyl,
R3b is hydrogen, halogen, fluoro-1–4C-alkyl, 1–4C-alkyl, 2–4C-alkenyl or 2–4C-alkynyl,
one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted alkoxy,
or in which
one of the substituents R4a and R4b on the one hand and one of the substituents R5a and R5b on the other hand is in each case hydrogen and the other substituents in each case together form a wholly or partially halogen-substituted 1–4C-alkylenedioxy radical,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is NH,
and their salts,
(d) compounds of the formula 1, in which
R1 is hydrogen, 1–4C-alkyl, 1–4C-alkoxy-1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen,
R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene,
where
R41 is a radical from which a hydroxy group is formed under physiological conditions,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene,
where
R51 is a radical from which a hydroxy group is formed under physiological conditions,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where one of the substituents R4a and R4b must have the meaning R41 and/or one of the substituents R5a and R5b must have the meaning R51 and/or where at least one of the substituents R4a, R4b, R5a and R5b must have the meaning 1–7C-alkyl, 2–7C-alkenyl, phenyl or phen-1–4C-alkyl and/or where either R4a and R4b or R5a and R5b together must be 1–7C-alkylidene,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is O (oxygen) or NH,
and their salts, and also
(e) compounds of the formula 1, in which
R1 is methyl,
R2 is methyl or hydroxymethyl, R3a is hydrogen, R3b is halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen and the other is hydroxyl, methoxy, ethoxy, propoxy, isopropoxy, butoxy, methoxyethoxy or methoxypropoxy, one of the substituents R5a and R5b is hydrogen and the other is hydrogen, hydroxyl, methoxy, ethoxy, propoxy, isopropoxy, butoxy, methoxyethoxy or methoxypropoxy, Arom is a phenyl radical, X is O (oxygen) or NH, and their salts.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and the methyl radical.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkyl-1–4C-alkyl represents one of the aforementioned 1–4C-alkyl radicals, which is substituted by one of the aforementioned 3–7C-cycloalkyl radicals. Examples which may be mentioned are the cyclopropylmethyl, the cyclohexylmethyl and the cyclohexylethyl radical.

1–4C-Alkoxy represents radicals, which in addition to the oxygen atom contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radical.

1–4C-Alkoxy-1–4C-alkyl represents one of the aforementioned 1–4C-alkyl radicals, which is substituted by one of the aforementioned 1–4C-alkoxy radicals. Examples which may be mentioned are the methoxymethyl, the methoxyethyl radical and the butoxyethyl radical.

1–4C-Alkoxycarbonyl (–CO-1–4C-alkoxy) represents a carbonyl group, to which one of the aforementioned 1–4C-alkoxy radicals is bonded. Examples which may be mentioned are the methoxycarbonyl ($CH_3O$—C(O)—) and the ethoxycarbonyl radical ($CH_3CH_2O$—C(O)—).

2–4C-Alkenyl represents straight-chain or branched alkenyl radicals having 2 to 4 carbon atoms. Examples which may be mentioned are the 2-butenyl, 3-butenyl, 1-propenyl and the 2-propenyl radical (allyl radical).

2–4C-Alkynyl represents straight-chain or branched alkynyl radicals having 2 to 4 carbon atoms. Examples which may be mentioned are the 2-butynyl, 3-butynyl, and preferably the 2-propynyl, radical (propargyl radical).

Fluoro-1–4C-alkyl represents one of the aforementioned 1–4C-alkyl radicals, which is substituted by one or more fluorine atoms. An example which may be mentioned is the trifluoromethyl radical.

Hydroxy-1–4C-alkyl represents aforementioned 1–4C-alkyl radicals, which are substituted by a hydroxy group. Examples which may be mentioned are the hydroxymethyl, the 2-hydroxyethyl and the 3-hydroxypropyl radical.

Halogen within the meaning of the invention is bromo, chloro and fluoro.

1–4C-Alkoxy-1–4C-alkoxy represents one of the aforementioned 1–4C-alkoxy radicals, which is substituted by a further 1–4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$-O—$CH_2$—$CH_2$—O—).

1–4C-Alkoxy-1–4C-alkoxy-1–4C-alkyl represents one of the aforementioned 1–4C-alkoxy-1–4C-alkyl radicals, which is substituted by one of the aforementioned 1–4C-alkoxy radicals. An example which may be mentioned is the radical 2-(methoxy)ethoxymethyl ($CH_3$-O—$CH_2$—$CH_2$-O—$CH_2$—).

Fluoro-1–4C-alkoxy-1–4C-alkyl represents one of the aforementioned 1–4C-alkyl radicals, which is substituted by a fluoro-1–4C-alkoxy radical. Fluoro-1–4C-alkoxy in this case represents one of the aforementioned 1–4C-alkoxy radicals, which is wholly or mainly substituted by fluorine. Examples of wholly or mainly fluoro-substituted 1–4C-alkoxy which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radical.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and the methyl radical.

2–7C-Alkenyl represents straight-chain or branched alkenyl radicals having 2 to 7 carbon atoms. Examples which may be mentioned are the 2-butenyl, 3-butenyl, 1-propenyl, the 2-propenyl (allyl) and the vinyl radical. The aforementioned 2–4C-alkenyl radicals are preferred.

Phen-1–4C-alkyl represents one of the aforementioned 1–4C-alkyl radicals, which is substituted by a phenyl radical. The phenethyl and in particular the benzyl radical are preferred.

Oxo-substituted 1–4C-alkoxy represents a 1–4C-alkoxy group, which instead of a methylene group contains a carbonyl group. An example which may be mentioned is the 2-oxopropoxy group.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkyl-1–4C-alkoxy represents one of the aforementioned 1–4C-alkoxy radicals, which is substituted by one of the aforementioned 3–7C-cycloalkyl radicals. Examples which may be mentioned are the cyclopropylmethoxy, the cyclobutylmethoxy and the cyclohexylethoxy radical.

Hydroxy-1–4C-alkoxy represents aforementioned 1–4C-alkoxy radicals, which are substituted by a hydroxy group. A preferred example which may be mentioned is the 2-hydroxyethoxy radical.

1–4C-Alkoxy-1–4C-alkoxy-1–4C-alkoxy represents one of the aforementioned 1–4C-alkoxy radicals, which is substituted by one of the aforementioned 1–4C-alkoxy-1–4C- alkoxy radicals. A preferred example which may be mentioned is the methoxyethoxyethoxy radical.

3–7C-Cycloalkoxy-1–4C-alkoxy represents one of the aforementioned 1–4C-alkoxy radicals, which is substituted by one of the aforementioned 3–7C-cycloalkoxy radicals. Examples which may be mentioned are the cyclopropoxymethoxy, the cyclobutoxymethoxy and the cyclohexyloxyethoxy radical.

3–7C-Cycloalkyl-1–4C-alkoxy-1–4C-alkoxy represents one of the aforementioned 1–4C-alkoxy radicals, which is substituted by one of the aforementioned 3–7C-cycloalkyl-1–4C-alkoxy radicals. Examples which may be mentioned are the cyclopropylmethoxyethoxy, the cyclobutylmethoxyethoxy and the cyclohexylethoxyethoxy radical.

1–4C-Alkylcarbonyl represents a radical, which in addition to the carbonyl group contains one of the aforementioned 1–4C-alkyl radicals. An example which may be mentioned is the acetyl radical.

1–4C-Alkylcarbonyloxy represents a 1–4C-alkylcarbonyl group which is bonded to an oxygen atom. An example which may be mentioned is the acetoxy radical ($CH_3CO-O-$).

Wholly or mainly halogen-substituted 1–4C-alkoxy which may primarily be mentioned are chloro- and/or in particular fluoro-substituted 1–4C-alkoxy radicals. Examples of halogen-substituted 1–4C-alkoxy which may be mentioned are the 2,2,2-trichloroethoxy, the hexachloroisopropoxy, the pentachloroisopropoxy, the 1,1,1-trichloro-3,3,3-trifluoro-2-propoxy, the 1,1,1-trichloro-2-methyl-2-propoxy, the 1,1,1-trichloro-2-propoxy, the 3-bromo-1,1,1-trifluoro-2-propoxy, the 3-bromo-1,1,1-trifluoro-2-butoxy, the 4-bromo-3,3,4,4-tetrafluoro-1-butoxy, the chlorodifluoromethoxy, the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radical.

1–7C-Alkylidene represents one of the aforementioned 1–7C-alkyl radicals, but which is bonded with a double bond. Examples which may be mentioned are isopropylidene (($CH_3)_2C=$) and in particular the methylene radical ($H_2C=$).

A radical R41 or R51 from which a hydroxy group is formed under physiological conditions is understood as meaning a radical —OR' from which the group R' is removed hydrolytically in the human or animal body with formation of the radicals —OH and the nontoxic compound R'OH. The radical R' can thus also be designated as a hydroxy protective group or as a "prodrug" radical. Such hydroxy protective groups or "prodrug" radicals are known, inter alia, from the patent applications and patents DE 4308095, WO 95/14016, EP 694547, WO 95/11884, WO 94/05282 and U.S. Pat. No. 5,432,183. Examples which can be mentioned are radicals R' having the general structure —C(O)R, —C(O)NRaRb, -P(O)ORaORb or —S(O)$_2$OR, where R, Ra and Rb represent any desired organic radicals or optionally hydrogen. In one embodiment of the invention, R41 and R51 have a common hydroxy protective group R', which can then have, for example, one of the structures —CRaRb—, —CRa(ORb)—, —C(ORa)(ORb)— or —P(O)OR—.

The groups to be mentioned as radicals R' to be emphasized by way of example in the context of the invention are
—C(O)—NR12R13,
—C(O)-alk-NR12R13,
—C(O)-alk-C(O)—NR12R13,
—P(O)(OH)$_2$,
—S(O)$_2$NR12R13,
—C(O)—R12,
—C(O)—C$_6$H$_3$R14R15,
—C(O)—OR12,
—C(O)-alk-C(O)—R12,
—C(O)-alk-C(O)—OR12,
—C(O)—C(O)—R12,
—C(O)—C(O)—OR12 and
—CH$_2$—OR12,
where
Alk is 1–7C-alkylene,
R12 is hydrogen, 1–7C-alkyl or 1–4C-alkyl substituted by halogen, carboxyl, hydroxyl, sulfo (—SO$_3$H), sulfamoyl (—SO$_2$NH$_2$), carbamoyl (—CONH$_2$), 1–4C-alkoxy or 1–4C-alkoxycarbonyl,
R13 is hydrogen or 1–4C-alkyl,
R14 is hydrogen, halogen, nitro, 1–4C-alkyl, 1–4C-alkoxy, 1–4C-alkoxycarbonyl, 1–4C-alkoxycarbonylamino, 1–4C-alkoxy-1–4C-alkoxycarbonylamino or trifluoromethyl and
R15 is hydrogen, halogen, 1–4C-alkyl or 1–4C-alkoxy.

1–7C-Alkylene represents straight-chain or branched 1–7C-alkylene radicals, for example the methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 1,2-dimethylethylene [—CH(CH$_3$)—CH(CH$_3$)—], 1,1-dimethylethylene [—C(CH$_3$)$_2$—CH$_2$-], 2,2-dimethylethylene [—CH$_2$—C(CH$_3$)$_2$—], isopropylidene [—C(CH$_3$)$_2$—], 1-methylethylene [—CH(CH$_3$)—CH$_2$—], pentamethylene (—CH$_2$CH$_2$CH$_2$CH$_2$CH$_2$—), hexamethylene (—CH$_2$CH$_2$CH$_2$CH$_2$CH$_2$CH$_2$—) and the heptamethylene radical (—CH$_2$CH$_2$CH$_2$CH$_2$CH$_2$CH$_2$CH$_2$—).

The groups to be mentioned as radicals R' to be particularly emphasized by way of example in this connection are —C(O)—N(CH$_3$)$_2$, —C(O)—N(C$_2$H$_5$)$_2$, —C(O)—NHC$_2$H$_5$, —C(O)—CH$_2$CH$_2$NH$_2$, —C(O)—(CH$_2$)$_3$NH$_2$, —C(O)—C(CH$_3$)$_2$NH$_2$, —C(O)—CH$_2$N(CH$_3$)$_2$, —C(O)—CH(NH$_2$)—CH(CH$_3$)$_2$, —C(O)—CH(NH$_2$)CH(CH$_3$)C$_2$H$_5$, —C(O)—(CH$_2$)$_8$C(O)N(CH$_3$)CH$_2$CH$_2$SO$_3$H, —P(O)(OH)$_2$, —S(O)$_2$NH$_2$, —C(O)—H, —C(O)—C(CH$_3$)$_3$, —C(O)—CH$_2$CH$_2$COOH, —C(O)—CH$_3$, —C(O)—C$_2$H$_5$, —C(O)—C$_6$H$_5$, —C(O)—C6H$_4$-4-NO$_2$, —C(O)—C$_6$H$_4$-3-NO$_2$, —C(O)—C$_6$H$_4$-4-OCH$_3$, —C(O)—C$_6$H$_4$-4-C(O)—OCH$_3$, —C(O)—OCH$_3$, —C(O)—O-menthyl, —C(O)—CH$_2$—C(O)—OCH$_3$, —C(O)—CH$_2$CH$_2$—C(O)—OCH$_3$, —C(O)—C(O)—OCH$_3$, —C(O)—C(O)—OC$_2$H$_5$ and —CH$_2$OCH(CH$_3$)$_2$, or (if R41 and R51 have a common hydroxy protective group) the groups —C(CH$_3$)$_2$—, —P(O)(OH)— and —CH[C(CH$_3$)$_3$]—.

With respect to the substituents R42 and R52, those which may be mentioned as exemplary radicals R6 and R7 are: methyl, ethyl, propyl, isopropyl, butyl, isobutyl, pentyl, difluoromethyl, 2,2,2-trifluoroethyl, 2-hydroxyethyl, 3-hydroxypropyl, methoxymethyl, methoxyethyl, ethoxymethyl, ethoxyethyl, carboxymethyl, carboxyethyl, carboxypropyl, methoxycarbonylmethyl, dimethylaminoethyl, diethylaminoethyl, phenyl, benzyl, 4-chlorophenyl, 4-aminophenyl, 4-chlorobenzyl, 4-difluoromethoxyphenyl, 4-trifluoromethoxyphenyl, 4-methylbenzyl, 3-methylbenzyl, 2,4-diaminophenyl, 2-methyl-4-tert-butylphenyl, 2-nitro-4-acetylphenyl, 4-fluorobenzyl, 4-nitrophenyl, 3-nitrophenyl, 3-aminophenyl, 2-methoxycarbonylamino-6-methylphenyl, 2-methoxyethoxycarbonylamino-6-methylphenyl, 2-methoxycarbonylamino-6-methylbenzyl and 2-methoxyethoxycarbonylamino-6-methylbenzyl.

Exemplary alkylene and alkenylene groups Alk1 and Alk2 in the substituents R42 and R52 which may be mentioned are: 1-methylethylene, 2-methylethylene, 1-phenylethylene, 2-phenylethylene, 1-propylpropylene, 3-propylpropylene, 2-aminopropylene, 2-tert-butyloxycarbonylaminopropylene, 2-hydroxypropylene, 2-oxopropylene, 2-carboxypropylene, 1-acetyl-1,2-dimethylethylene, 2-acetyl-1,2-dimethylethylene, 1,1-dimethyl-2-oxoethylene, 1-oxo-2,2-dimethylethylene, 1,3-dioxobutylene, 2,4-dioxobutylene, 1,2-dioxopropylene, 2,3dioxopropylene, prop-1-enylene, prop-2-enylene, but-1-enylene, but-2-enylene, but-3-enylene, but-4-enylene, buta-1,3-dienylene, buta-2,4-dienylene, 1-oxobut-2-enylene, 4-oxobut-2-enylene, 1-oxo-2,2-difluoroethylene, 2-oxo-1,1-difluoroethylene, 1-oxopropylene, 3-oxopropylene, 1-carboxyethylene and 2-carboxyethylene.

Halo-1–4C-alkyl represents one of the aforementioned 1–4C-alkyl radicals, which is substituted by one of the aforementioned halogen atoms. An example which may be mentioned is the 3-chloropropyl radical.

Carboxy-1–4C-alkyl for example represents the carboxymethyl (—CH$_2$COOH) or the carboxyethyl radical (—CH$_2$CH$_2$COOH).

1–4C-Alkoxycarbonyl-1–4C-alkyl represents one of the aforementioned 1–4C-alkyl radicals, which is substituted by one of the aforementioned 1–4C-alkoxycarbonyl radicals. An example which may be mentioned is the ethoxycarbonylmethyl radical (CH$_3$CH$_2$OC(O)CH$_2$—).

Di-1–4C-alkylamino represents an amino radical, which is substituted by two identical or different radicals from the aforementioned 1–4C-alkyl radicals. Examples which may be mentioned are the dimethylamino, the diethylamino and the diisopropylamino radical.

Di-1–4C-alkylamino-1–4C-alkyl represents one of the aforementioned 1–4C-alkyl radicals, which is substituted by one of the aforementioned di-1–4C-alkylamino radicals. Examples which may be mentioned are the dimethylaminomethyl, the dimethylaminoethyl and the diethylaminoethyl radical.

Ar-1–4C-Alkyl represents one of the aforementioned, Ar-substituted 1–4C-alkyl radicals, where Ar has the aforementioned meaning. Examples which may be mentioned are the phenethyl and the benzyl radical.

1–4C-Alkylcarbonyl represents a radical, which in addition to the carbonyl group contains one of the aforementioned 1–4C-alkyl radicals. An example which may be mentioned is the acetyl radical.

1–4C-Alkoxycarbonylamino represents an amino radical, which is substituted by one of the aforementioned 1–4C-alkoxycarbonyl radicals. Examples which may be mentioned are the ethoxycarbonylamino and the methoxycarbonylamino radical.

1–4C-Alkoxy-1–4C-alkoxycarbonyl represents a carbonyl group, to which one of the aforementioned 1–4C-alkoxy-1–4C-alkoxy radicals is bonded. Examples which may be mentioned are the 2-(methoxy)-ethoxycarbonyl (CH$_3$—O—CH$_2$CH$_2$—O—CO—) and the 2-(ethoxy) ethoxycarbonyl radical (CH$_3$CH$_2$—O—CH$_2$CH$_2$—O—CO—).

1–4C-Alkoxy-1–4C-alkoxycarbonylamino represents an amino radical, which is substituted by one of the aforementioned 1–4C-alkoxy-1–4C-alkoxycarbonyl radicals. Examples which may be mentioned are the 2-(methoxy) ethoxycarbonylamino and the 2-(ethoxy) ethoxycarbonylamino radical.

2–7C-Alkylene represents straight-chain or branched 2–7C-alkylene radicals, for example the ethylene (—CH$_2$—CH$_2$—), trimethylene (—CH$_2$—CH$_2$—CH$_2$—), tetramethylene (—CH$_2$—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—], 1-methylethylene [—CH(CH$_3$)—CH$_2$—], pentamethylene (—CH$_2$—CH$_2$—CH$_2$—CH$_2$—CH$_2$—), hexamethylene (—CH$_2$—CH$_2$—CH$_2$—CH$_2$—CH$_2$—CH$_2$—) and the heptamethylene radical (—CH$_2$—CH$_2$—CH$_2$—CH$_2$—CH$_2$—CH$_2$—CH$_2$—).

3–4C-Alkenylene represents straight-chain 3–4C-alkenylene radicals, for example the 1-propenylene, the 2-propenylene, the 2-butenylene and the 3-butenylene radical.

1–4C-Alkylenedioxy radicals which, if desired, are wholly or partially halogen-substituted and which may be mentioned are, for example, the methylenedioxy (—O—CH$_2$—O—), the ethylenedioxy (—O—CH$_2$—CH$_2$—O—) or the propylenedioxy radical (—O—CH$_2$—CH$_2$—CH$_2$—O—) as unsubstituted radicals, of the halogen-substituted radicals, in particular fluoro-substituted 1–2C-alkylenedioxy, for example the difluoroethylenedioxy (—O—CF$_2$—CH$_2$—O—), the tetrafluorethylenedioxy (—O—CF$_2$—CF$_2$—O—) and in particular the difluoromethylenedioxy (—O—CF$_2$—O—), and the 1,1,2-trifluoroethylenedioxy radical (—O—CF$_2$CHF—O—) and also the chlorotrifluoroethylenedioxy radical, may be mentioned.

2–4C-Alkenyloxy represents a radical, which in addition to the oxygen atom contains a 2–4C-alkenyl radical. An example which may be mentioned is the allyloxy radical.

Aryl-1–4C-alkyl represents an aryl-substituted 1–4C-alkyl radical. An example which may be mentioned is the benzyl radical.

Aryl-1–4C-alkoxy represents an aryl-substituted 1–4C-alkoxy radical. An example which may be mentioned is the benzyloxy radical.

Mono- or di-1–4C-alkylamino radicals contain, in addition to the nitrogen atom, one or two of the aforementioned 1–4C-alkyl radicals. Di-1–4C-alkylamino is preferred and here, in particular, dimethyl-, diethyl- or diisopropylamino.

1–4C-Alkylcarbonylamino represents an amino group to which a 1–4C-alkylcarbonyl radical is bonded. Examples which may be mentioned are the propionylamino (C$_3$H$_7$C (O)NH—) and the acetylamino radical (acetamido radical) (CH$_3$C(O)NH—).

Arom radicals which may be mentioned are, for example, the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5-bis(trifluoromethyl)phenyl, 4-butoxyphenyl, 2-chlorophenyl, 3-chlorophenyl, 4-chlorophenyl, 2-chloro-6-fluorophenyl, 3-chloro-4-fluorophenyl, 2-chloro-5-nitrophenyl, 4-chloro-3-nitrophenyl, 3-(4-chlorophenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrrolyl, 3,4-dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-dibromo-5-methyl-2-pyrrolyl, 2,5-dimethyl-1-phenyl-3-pyrrolyl, 5-carboxy-3-ethyl-4-methyl-2-pyrrolyl, 3,5-dimethyl-2-pyrrolyl, 2,5-dimethyl-1-(4-trifluoromethylphenyl)-3-pyrrolyl, 1-(2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-trifluoromethoxyphenyl)-2-pyrrolyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluoromethyl-4-pyrazolyl, 1-(4-chlorobenzyl)-5-pyrazolyl, 1,3-dimethyl-5-(4-chlorophenoxy)-4-pyrazolyl, 1-methyl-3-trifluoromethyl-5-(3-trifluoromethylphenoxy)-4-pyrazolyl, 4-methoxycarbonyl-1-(2,6-dichlorophenyl)-5-pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imidazolyl, 4-bromo-1-methyl-5-imidazolyl, 2-butylimidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluoromethoxyphenyl)-2-furyl, 5-(4-methoxy-2-nitrophenyl)-2-furyl, 4-bromo-2-furyl, 5-dimethylamino-2-furyl, 5-bromo-2-furyl, 5-sulfo-2-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxy-2-thienyl, 2,5-dichloro-3-thienyl, 3-methoxy-2-thienyl, 2-benzothienyl, 3-methyl-2-benzothienyl, 2-bromo-5-chloro-3-benzothienyl, 2-thiazolyl, 2-amino-4-chloro-5-thiazolyl, 2,4-dichloro-5-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4-(4-chlorophenyl)-3-pyridyl, 2-chloro-5-methoxy-carbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidinyl, 2-quinolinyl, 3-quinolinyl, 4-quinolinyl, 2-chloro-3-quinolinyl, 2-chloro-6-methoxy-3-quinolinyl, 8-hydroxyl-2-quinolinyl and 4-isoquinolinyl.

Possible salts of compounds of the formula I—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are used in salt preparation—depending on whether a mono- or polybasic acid is concerned and on which salt is desired—in an equimolar quantitative ratio or one differing therefrom.

Pharmacologically intolerable salts, which can initially be obtained, for example, as process products in the production of the compounds according to the invention on the industrial scale, are converted into the pharmacologically tolerable salts by processes known to the person skilled in the art.

It is known to the person skilled in the art that the compounds according to invention and their salts, if, for example, they are isolated in crystalline form, can contain various amounts of solvents. The invention therefore also comprises all solvates and in particular all hydrates of the compounds of the formula I, and also all solvates and in particular all hydrates of the salts of the compounds of the formula I.

The compounds of the formula I have up to three chiral centers in the parent structure. The invention thus relates to all conceivable stereoisomers in any desired mixing ratio to one another, including the pure enantiomers, which are a preferred subject of the invention.

One embodiment (embodiment 1) of the invention are compounds of the formula 1, in which R1 is hydrogen, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R2, R3a, R3b, Arom and X have the meanings indicated at the outset, and their salts.

A further embodiment (embodiment 2) are compounds of the formula 1, in which

R1 is hydrogen, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl, one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen), where one of the substituents R4a and R4b must be the radical R42 and/or one of the substituents R5a and R5b must be the radical R52, and in which R2, R3a, R3b, R42, R52, Arom and X have the meanings indicated at the outset, and their salts.

A further embodiment (embodiment 3) are compounds of the formula 1, in which one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen), where one of the substituents R4a and R4b must be the radical R42 and/or one of the substituents R5a and R5b must be the radical R52, X is O (oxygen), and in which R1, R2, R3a, R3b, R42, R52 and Arom have the meanings indicated at the outset, and their salts.

A further embodiment (embodiment 4) of the invention are compounds of the formula 1, in which R1 is 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl or fluoro-1–4C-alkyl, one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted 1–4C-alkoxy, or in which one of the substituents R4a and A4b on the one hand and one of the substituents R5a and R5b on the other hand is in each case hydrogen and the other substituents in each case together form a wholly or partially halogen-substituted 1–4C-alkylenedioxy radical, and in which R2, R3a, R3b, Arom and X have the meanings indicated at the outset, and their salts.

A further embodiment (embodiment 5) are compounds of the formula 1, in which one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted 1–4C-alkoxy, or in which one of the substituents R4a and R4b on the one hand and one of the substituents R5a and R5b on the other hand is in each case hydrogen and the other substituents in each case together form a wholly or partially halogen-substituted 1–4C-alkylenedioxy radical, X is O (oxygen).

and in which R1, R2, R3a, R3b and Arom have the meanings indicated at the outset, and their salts.

A further embodiment (embodiment 6) are compounds of the formula 1, in which

R1 is 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl or fluoro-1–4C-alkyl, one of the substituents R4a and R4b is hydrogen and the other is hydroxyl, 1–4C-alkoxy, 1–4C-alkoxy-1–4C-alkoxy, 1–4C-alkylcarbonyloxy or the radical R41, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, where one of the substituents R4a and R4b must be the radical R41 and/or one of the substituents R5a and R5b must be the radical R51, and in which R2, R3a, R3b, R41, R51, Arom and X have the meanings indicated at the outset, and their salts.

A further embodiment (embodiment 7) are compounds of the formula 1, in which

R1 is 3–7C-cycloalkyl, 3–7C-cycloalkyl-1–4C-alkyl, 1–4C-alkoxy, 1–4C-alkoxycarbonyl, 2–4C-alkenyl, 2–4C-alkynyl or fluoro-1–4C-alkyl, one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, where at least one of the substituents R4a, R4b, R5a and R5b must have the meaning 1–7C-alkyl, 2–7C-alkenyl, phenyl or phen-1–4C-alkyl or where either R4a and R4b or R5a and R5b together must be 1–7C-alkylidene, and in which R2, R3a, R3b, Arom and X have the meanings indicated at the outset, and their salts.

A further embodiment (embodiment 8) are compounds of the formula 1, in which

R1 is hydrogen, 2–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl, R3a is hydrogen, R3b is halogen, trifluoromethyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R2, R31, R32, Arom and X have the meanings indicated at the outset, and their salts.

A further embodiment (embodiment 9) of the invention are compounds of the formula 1, in which R2 is hydrogen, aryl, 3–7C-cycloalkyl, 3–7C-cycloalkyl-1–4C-alkyl, 1–4C-alkoxycarbonyl, halogen, 2–4C-alkenyl, 2–4C-alkynyl, fluoro-1–4C-alkyl or cyanomethyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R3a, R3b, Arom and X have the meanings indicated at the outset, and their salts.

A further embodiment (embodiment 10) are compounds of the formula 1, in which

R2 is hydrogen, aryl, 3–7C-cycloalkyl, 3–7C-cycloalkyl-1–4C-alkyl, 1–4C-alkoxycarbonyl, halogen, 2–4C-alkenyl, 2–4C-alkynyl, fluoro-1–4C-alkyl or cyanomethyl, one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen), where one of the substituents R4a and R4b must be the radical R42 and/or one of the substituents R5a and R5b must be the radical R52, and in which R1, R3a, R3b, R42, R52, Arom and X have the meanings indicated at the outset, and their salts.

A further embodiment (embodiment 11) of the invention are compounds of the formula 1, in which R2 is aryl, 3–7C-cycloalkyl, 3–7C-cycloalkyl-1–4C-alkyl, 1–4C-alkoxycarbonyl, fluoro-1–4C-alkyl or cyanomethyl, one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted 1–4C-alkoxy, or in which one of the substituents R4a and R4b on the one hand and one of the substituents R5a and R5b on the other hand is in each case hydrogen and the other substituents in each case together form a wholly or partially halogen-substituted 1–4C-alkylenedioxy radical, and in which R1, R3a, R3b, Arom and X have the meanings indicated at the outset, and their salts.

A further embodiment (embodiment 12) are compounds of the formula 1, in which

R2 is aryl, 3–7C-cycloalkyl, 3–7C-cycloalkyl-1–4C-alkyl, 1–4C-alkoxycarbonyl, fluoro-1–4C-alkyl or cyanomethyl, one of the substituents R4a and R4b is hydrogen and the other is hydroxyl, 1–4C-alkoxy, 1–4C-alkoxy-1–4C-alkoxy, 1–4C-alkylcarbonyloxy or the radical R41, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, where one of the substituents R4a and R4b must be the radical R41 and/or one of the substituents R5a and R5b must be the radical R51, and in which R1, R3a, R3b, R41, R51, Arom and X have the meanings indicated at the outset, and their salts.

A further embodiment (embodiment 13) are compounds of the formula 1, in which

R2 is aryl, 3–7C-cycloalkyl, 3–7C-cycloalkyl-1–4C-alkyl, 1–4C-alkoxycarbonyl, fluoro-1–4C-alkyl or cyanomethyl, one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, where at least one of the substituents R4a, R4b, R5a and R5b must have the meaning 1–7C-alkyl, 2–7C-alkenyl, phenyl or phen-1–4C-alkyl or where either R4a and R4b or R5a and R5b together must be 1–7C-alkylidene, and in which R1, R3a, R3b, Arom and X have the meanings indicated at the outset, and their salts.

A further embodiment (embodiment 14) are compounds of the formula 1, in which
R2 is hydrogen, 2–4C-alkyl, aryl, 3–7C-cycloalkyl, 3–7C-cycloalkyl-1–4C-alkyl, 1–4C-alkoxycarbonyl, hydroxy-2–4C-alkyl, halogen, 2–4C-alkenyl, 2–4C-alkynyl, fluoro-1–4C-alkyl or cyanomethyl, R3a is hydrogen, R3b is halogen, trifluoromethyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which
one of the substituents R4a and R4b on the one hand and one of the substituents R5a and R5b on the other hand is in each case hydrogen and the other substituents in each case together form a 1–4C-alkylenedioxy radical, and in which R1, R31, R32, Arom and X have the meanings indicated at the outset, and their salts.

A further embodiment (embodiment 15) of the invention are compounds of the formula 1, in which
R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where at least one of the substituents R3a and R3b must have a meaning other than hydrogen and halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which
one of the substituents R4a and R4b on the one hand and one of the substituents R5a and R5b on the other hand is in each case hydrogen and the other substituents in each case together form a 1–4C-alkylenedioxy radical, and in which R1, R2, R31, R32, Arom and X have the meanings indicated at the outset, and their salts, where compounds of the formula 1 are excluded, in which
R1 is methyl,
R2 is methyl or hydroxymethyl,
R3a is hydrogen,
R3b is halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl, or where
R31 and R32 together, including the nitrogen atom to which both are bonded, are a pyrrolidino, piperidino or morpholino radical, one of the substituents R4a and R4b is hydrogen and the other is hydroxyl, methoxy, ethoxy, propoxy, isopropoxy, butoxy, methoxyethoxy or methoxypropoxy, one of the substituents R5a and R5b is hydrogen and the other is hydrogen, hydroxyl, methoxy, ethoxy, propoxy, isopropoxy, butoxy, methoxyethoxy or methoxypropoxy, Arom is a phenyl radical,
X is O (oxygen) or NH,
and their salts.

A further embodiment (embodiment 16) are compounds of the formula 1, in which
R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where at least one of the substituents R3a and R3b must have a meaning other than hydrogen and halogen, one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen), where one of the substituents R4a and R4b must be the radical R42 and/or one of the substituents R5a and R5b must be the radical R52, and in which R1, R2, R31, R32, R42, R52, Arom and X have the meanings indicated at the outset,
and their salts.

A further embodiment (embodiment 17) of the invention are compounds of the formula 1, in which R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where at least one of the substituents R3a and R3b must have a meaning other than hydrogen, halogen, trifluoromethyl, 1–4C-alkyl, 2–4C-alkenyl and 2–4C-alkynyl, one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted 1–4C-alkoxy, or in which one of the substituents R4a and R4b on the one hand and one of the substituents R5a and R5b on the other hand is in each case hydrogen and the other substituents in each case together form a wholly or partially halogen-substituted 1–4C-alkylenedioxy radical, and in which R1, R2, R31, R32, Arom and X have the meanings indicated at the outset,
and their salts.

A further embodiment (embodiment 18) are compounds of the formula 1, in which

R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where—if R3a is hydrogen—R3b must have the meaning 1–4C-alkoxy-1–4C-alkoxy-1–4C-alkyl, one of the substituents R4a and R4b is hydrogen and the other is hydroxyl, 1–4C-alkoxy, 1–4C-alkoxy-1–4C-alkoxy, 1–4C-alkylcarbonyloxy or the radical R41, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, where one of the substituents R4a and R4b must be the radical R41 and/or one of the substituents R5a and R5b must be the radical R51, and in which R1, R2, R31, R32, R41, R51, Arom and X have the meanings indicated at the outset,
and their salts.

A further embodiment (embodiment 19) are compounds of the formula 1, in which

R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where—if R3a is hydrogen—R3b must have the meaning 1–4C-alkoxy-1–4C-alkoxy-1–4C-alkyl, one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, where at least one of the substituents R4a, R4b, R5a and R5b must have the meaning 1–7C-alkyl, 2–7C-alkenyl, phenyl or phen-1–4C-alkyl or where either R4a and R4b or R5a and R5b together must be 1–7C-alkylidene, and in which R1, R2, R31, R32, Arom and X have the meanings indicated at the outset,
and their salts.

A further embodiment (embodiment 20) are compounds of the formula 1, in which

R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where—if R3a is hydrogen—R3b must have the meaning trifluoromethyl, 1–4C-alkyl, 2–4C-alkenyl or 2–4C-alkynyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R2, R31, R32, Arom and X have the meanings indicated at the outset, and their salts.

A further embodiment (embodiment 21) of the invention are compounds of the formula 1, in which one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R8, R9, R10, R11 and X have the meanings indicated at the outset, and their salts.

A further embodiment (embodiment 22) are compounds of the formula 1, in which one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen), where one of the substituents R4a and R4b must be the radical R42 and/or one of the substituents R5a and R5b must be the radical R52, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R42, R52, R8, R9, R10, R11 and X have the meanings indicated at the outset, and their salts.

A further embodiment (embodiment 23) of the invention are compounds of the formula 1, in which one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least one of the substituents R4a, R4b, R5a and R5b is wholly or mainly halogen-substituted 1–4C-alkoxy, or in which one of the substituents R4a and R4b on the one hand and one of the substituents R5a and R5b on the other hand is in each case hydrogen and the other substituents in each case together form a wholly or partially halogen-substituted 1–4C-alkylenedioxy radical, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R8, R9, R10, R11 and X have the meanings indicated at the outset, and their salts.

A further embodiment (embodiment 24) are compounds of the formula 1, in which one of the substituents R4a and R4b is hydrogen and the other is hydroxyl, 1–4C-alkoxy, 1–4C-alkoxy-1–4C-alkoxy, 1–4C-alkylcarbonyloxy or the radical R41, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, where one of the substituents R4a and R4b must be the radical R41 and/or one of the substituents R5a and R5b must be the radical R51, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R41, R51, R8, R9, R10, R11 and X have the meanings indicated at the outset, and their salts.

A further embodiment (embodiment 25) are compounds of the formula 1, in which one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene, or in which one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, where at least one of the substituents R4a, R4b, R5a and R5b must have the meaning 1–7C-alkyl, 2–7C-alkenyl, phenyl or phen-1–4C-alkyl or where either R4a and R4b or R5a and R5b together must be 1–7C-alkylidene, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R8, R9, R10, R11 and X have the meanings indicated at the outset, and their salts.

A further embodiment (embodiment 26) are compounds of the formula 1, in which

R3a is hydrogen,

R3b is halogen, trifluoromethyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, one of the substituents R4a and R4b is hydrogen and the other is hydroxyl, 1–4C-alkoxy, 1–4C-alkoxy-1–4C-alkoxy or 1–4C-alkylcarbonyloxy is, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl and R8, R9, R10 and R11 in each case are hydrogen, and in which R1, R2, R8, R9, R10, R11 and X have the meanings indicated at the outset, and their salts.

A further embodiment (embodiment 27) are compounds of the formula 1, in which

R1 is 3–7C-cycloalkyl, 3–7C-cycloalkyl-1–4C-alkyl, 1–4C-alkoxy, 1–4C-alkoxycarbonyl, 2–4C-alkenyl, 2–4C-alkynyl or fluoro-1–4C-alkyl, and in which R2, R3a, R3b, R4a, R4b, R5a, R5b, Arom and X have the meanings indicated at the outset, and their salts.

A further embodiment (embodiment 28) are compounds of the formula 1, in which

R2 is aryl, 3–7C-cycloalkyl, 3–7C-cycloalkyl-1–4C-alkyl, 1–4C-alkoxycarbonyl, fluoro-1–4C-alkyl or cyanomethyl, and in which R1, R3a, R3b, R4a, R4b, R5a, R5b, Arom and X have the meanings indicated at the outset, and their salts.

A further embodiment (embodiment 29) are compounds of the formula 1, in which one of the substituents R4a and R4b and/or one of the substituents R5a and R5b have the meaning oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy-1–4C-alkoxy, 3–7C-cycloalkoxy-1–4C-alkoxy or 3–7C-cycloalkyl-1–4C-alkoxy-1–4C-alkoxy, and in which R1, R2, R3a, R3b, Arom and X have the meanings indicated at the outset, and their salts.

A further embodiment (embodiment 30) are compounds of the formula 1, in which

Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R4a, R4b, R5a, R5b, R8, R9, R10, R11 and X have the meanings indicated at the outset, and their salts.

A further embodiment (embodiment 31) of the invention are compounds of the formula 1, in which R2 is hydrogen or fluoro-1–4C-alkyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R3a, R3b, Arom and X have the meanings indicated at the outset, and their salts.

A further embodiment (embodiment 32) of the invention are compounds of the formula 1, in which R2 is halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R3a, R3b, Arom and X have the meanings indicated at the outset, and their salts.

Compounds to be emphasized are those of the formula 1, in which

R1 is hydrogen, 1–4C-alkyl, 3–7C-cycloalkyl, 1–4C-alkoxy-1–4C-alkyl, 2–4C-alkynyl or fluoro-1–4C-alkyl, R2 is hydrogen, 1–4C-alkyl, aryl, hydroxy-1–4C-alkyl, halogen, 2–4C-alkenyl, 2—4C-alkynyl or fluoro-1–4C-alkyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen or 1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen or 1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy or 1–4C-alkoxy-1–4C-alkoxy-1–4C-alkoxy, or in which R5a and R5b together are O (oxygen), Arom is a mono- or bicyclic aromatic radical substituted by R8, R9, R10 and R11, which is selected from the group consisting of phenyl, furanyl (furyl) and thiophenyl (thienyl), where R8 is hydrogen, 1–4C-alkyl, hydroxy-1–4C-alkyl, 1–4C-alkoxy, 1–4C-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl, R9 is hydrogen, 1–4C-alkyl, 1–4C-alkoxy, 1–4C-alkoxycarbonyl, halogen, trifluoromethyl or hydroxyl, R10 is hydrogen and R11 is hydrogen, X is O (oxygen) or NH, and their salts, where the following are excluded (a) compounds of the formula 1, in which R1 is 1–4C-alkyl, R2 is 1–4C-alkyl or hydroxy-1–4C-alkyl, R3a is hydrogen, R3b is hydrogen or halogen, one of the substituents R4a and R4b is hydrogen and the other is hydroxyl, 1–4C-alkoxy or 1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, or in which R5a and R5b together are O (oxygen), Arom is phenyl substituted by R8, R9, R10 and R11, where R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino, R9 is hydrogen, 1–4C-alkyl, 1–4C-alkoxy or halogen, R10 is hydrogen and R11 is hydrogen, X is O (oxygen) or NH, and their salts, (b) compounds of the formula 1, in which R1 is hydrogen, 1–4C-alkyl or 1–4C-alkoxy-1–4C-alkyl, R2 is hydrogen, 1–4C-alkyl, hydroxy-1–4C-alkyl, halogen, 2–4C-alkenyl or 2–4C-alkynyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen or 1–4C-alkyl and the other is hydroxyl, 1–4C-alkoxy or 1–4C-alkoxy-1–4C-alkoxy, or in which R4a and R4b together are O (oxygen), one of the substituents R5a and R5b is hydrogen or 1–4C-alkyl and the other is hydrogen, hydroxyl, 1–4C-alkoxy or 1–4C-alkoxy-1–4C-alkoxy, or in which R5a and R5b together are O (oxygen), where at least one of the substituents R4a, R4b, R5a and R5b must have the meaning 1–4C-alkyl, Arom is phenyl substituted by R8, R9, R10 and R11, where R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino, R9 is hydrogen, 1–4C-alkyl, 1–4C-alkoxy or halogen, R10 is hydrogen and R11 is hydrogen, X is O (oxygen) or NH, and their salts, and also (c) compounds of the formula 1, in which R1 is methyl, R2 is methyl or hydroxymethyl, R3a is hydrogen, R3b is halogen or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen and the other is hydroxyl, methoxy, ethoxy, propoxy, isopropoxy, butoxy, methoxyethoxy or methoxypropoxy, one of the substituents R5a and R5b is hydrogen and the other is hydrogen, hydroxyl, methoxy, ethoxy, propoxy, isopropoxy, butoxy, methoxyethoxy or methoxypropoxy, Arom is a phenyl radical and X is O (oxygen) or NH, and their salts.

Compounds to be particularly emphasized are those of the formula 1, in which

R1 is 1–4C-alkyl or 1–4C-alkoxy-1–4C-alkyl,

R2 is hydrogen, 1–4C-alkyl, phenyl, hydroxy-1–4C-alkyl or halogen,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, and their salts, where the following are excluded compounds of the formula 1, in which R1 is 1–4C-alkyl, R2 is 1–4C-alkyl or hydroxy-1–4C-alkyl, R3a is hydrogen, R3b is hydrogen, one of the substituents R4a and R4b is hydrogen and the other is hydroxyl, 1–4C-alkoxy or 1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, X is O (oxygen) or NH, and their salts.

Compounds of embodiment 28 to be particularly emphasized are those of the formula 1, in which R1 is 1–4C-alkyl or 1–4C-alkoxy-1–4C-alkyl, R2 is phenyl, R3a is hydrogen, R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, and their salts.

Compounds of embodiment 29 to be particularly emphasized are those of the formula 1, in which R1 is 1–4C-alkyl or 1–4C-alkoxy-1–4C-alkyl, R2 is hydrogen, 1–4C-alkyl, phenyl, hydroxy-1–4C-alkyl or halogen, R3a is hydrogen, R3b is hydrogen, one of the substituents R4a and R4b and/or one of the substituents R5a and R5b have the meaning hydroxy-1–4C-alkoxy or 1–4C-alkoxy-1–4C-alkoxy-1–4C-alkoxy, Arom is phenyl, furanyl (furyl) or thiophenyl (thienyl), X is O (oxygen) or NH, and their salts.

Compounds of embodiment 30 to be particularly emphasized are those of the formula 1, in which R1 is 1–4C-alkyl or 1–4C-alkoxy-1–4C-alkyl, R2 is hydrogen, 1–4C-alkyl, phenyl, hydroxy-1–4C-alkyl or halogen, R3a is hydrogen, R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is furanyl (furyl) or thiophenyl (thienyl), X is O (oxygen) or NH, and their salts.

Compounds of embodiment 31 to be particularly emphasized are those of the formula 1, in which R1 is 1–4C-alkyl or 1–4C-alkoxy-1–4C-alkyl, R2 is hydrogen, R3a is hydrogen, R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, and their salts.

Compounds of embodiment 32 to be particularly emphasized are those of the formula 1, in which R1 is 1–4C-alkyl or 1–4C-alkoxy-1–4C-alkyl, R2 is halogen, R3a is hydrogen, R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, and their salts.

Among the compounds according to the invention, including the embodiments 1 to 32 and the compounds to be emphasized and to be particularly emphasized, the optically pure compounds of the formula 1*

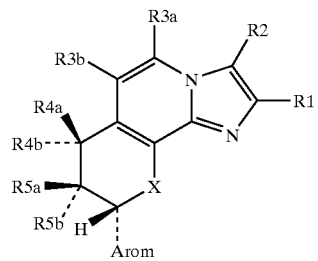
(1*)

are preferred, those with R5b=hydrogen being particularly preferred.

Preferred compounds of the formula 1* are those in which

R1 is 1–4C-alkyl or 1–4C-alkoxy-1–4C-alkyl,

R2 is hydrogen, 1–4C-alkyl, phenyl, hydroxy-1–4C-alkyl or halogen,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, R5a is hydrogen, hydroxyl, 1–4C-alkoxy or 1–4C-alkoxy-1–4C-alkoxy, R5b is hydrogen, Arom is phenyl, furanyl (furyl) or thiophenyl (thienyl), X is O (oxygen) or NH, and their salts, where the following are excluded compounds of the formula 1, in which R1 is 1–4C-alkyl, R2 is 1–4C-alkyl or hydroxy-1–4C-alkyl, R3a is hydrogen, R3b is hydrogen, one of the substituents R4a and R4b is hydrogen and the other is hydroxyl, 1–4C-alkoxy or 1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, X is O (oxygen) or NH, and their salts.

Compounds with exemplary substituents to be particularly emphasized are those of the formula 1*, in which R1 is hydrogen, methyl, cyclopropyl, methoxymethyl or trifluoromethyl, R2 is hydrogen, methyl, phenyl, hydroxymethyl, chloro, bromo, ethynyl, or trifluoromethyl, R3a is hydrogen, R3b is hydrogen, fluorine, methyl or the radical —CO—N(CH$_3$)$_2$, one of the substituents R4a and R4b is hydrogen and the other is hydroxyl, methoxy, ethoxy, propoxy, isopropoxy, butoxy, hydroxyethoxy, methoxyethoxy, methoxypropoxy, methoxyethoxyethoxy, 2-oxopropoxy, cyclopropyloxy or cyclopropylmethoxy, R5a is hydrogen, hydroxyl, methoxy, ethoxy, propoxy, isopropoxy, butoxy, methoxyethoxy, methoxypropoxy, methoxyethoxyethoxy, 2-oxopropoxy, cyclopropyloxy or cyclopropylmethoxy, R5b is hydrogen,
Arom is a phenyl radical and
X is O (oxygen) or NH,
and their salts,
where the following are excluded
(a) compounds of the formula 1*, in which
R1 is methyl,
R2 is methyl or hydroxymethyl,
R3a is hydrogen,
R3b is hydrogen,
one of the substituents R4a and R4b is hydrogen and the other is hydroxyl, methoxy, ethoxy, propoxy, isopropoxy, butoxy, methoxyethoxy or methoxypropoxy,
R5a is hydrogen, hydroxyl, methoxy, ethoxy, propoxy, isopropoxy, butoxy, methoxyethoxy or methoxypropoxy,
R5b is hydrogen,
Arom is a phenyl radical and
X is O (oxygen) or NH,
and their salts, and
(b) compounds of the formula 1*, in which
R1 is methyl,
R2 is methyl or hydroxymethyl,
R3a is hydrogen,
R3b is fluorine or the radical —CO—N(CH$_3$)$_2$,
one of the substituents R4a and R4b is hydrogen and the other is hydroxyl, methoxy, ethoxy, propoxy, isopropoxy, butoxy, methoxyethoxy or methoxypropoxy,
R5a is hydrogen, hydroxyl, methoxy, ethoxy, propoxy, isopropoxy, butoxy, methoxyethoxy or methoxypropoxy,
R5b is hydrogen,
Arom is a phenyl radical and
X is O (oxygen) or NH,
and their salts.

Preferred exemplary compounds of the formula 1* are those, in which
R1 is methyl or methoxymethyl,
R2 is hydrogen, methyl, phenyl, hydroxymethyl, chloro or bromo,
R3a is hydrogen,
R3b is hydrogen,
one of the substituents R4a and R4b is hydrogen and the other is hydroxyl, methoxy, ethoxy, hydroxyethoxy, methoxyethoxy or methoxyethoxyethoxy,
R5a is hydrogen, hydroxyl or methoxyethoxy,
R5b is hydrogen,
Arom is a phenyl radical and
X is O (oxygen) or NH,
and their salts,
where the following are excluded
compounds of the formula 1*, in which
R1 is methyl,
R2 is methyl or hydroxymethyl,
R3a is hydrogen,
R3b is hydrogen,
one of the substituents R4a and R4b is hydrogen and the other is hydroxyl, methoxy, ethoxy or methoxyethoxy,
R5a is hydrogen, hydroxyl or methoxyethoxy,
R5b is hydrogen,
Arom is a phenyl radical and
X is O (oxygen) or NH,
and their salts.

Particularly preferred are the compounds given as final products in the examples, and their salts, including those intermediates which are within the scope of the invention, and their salts.

The compounds according to the invention can thus be prepared as described by way of example in the following examples below, or starting from corresponding starting compounds using analogous process steps (see, for example, WO 98/42707, WO 98/54188, WO00/17200 and WO00/26217), or as outlined very generally in the following schemes.

Scheme 1:

Preparation of compounds 1 where X=NH, R4a or R4b=hydroxyl, R5a/R5b=H and any desired substituents R3a and R3b

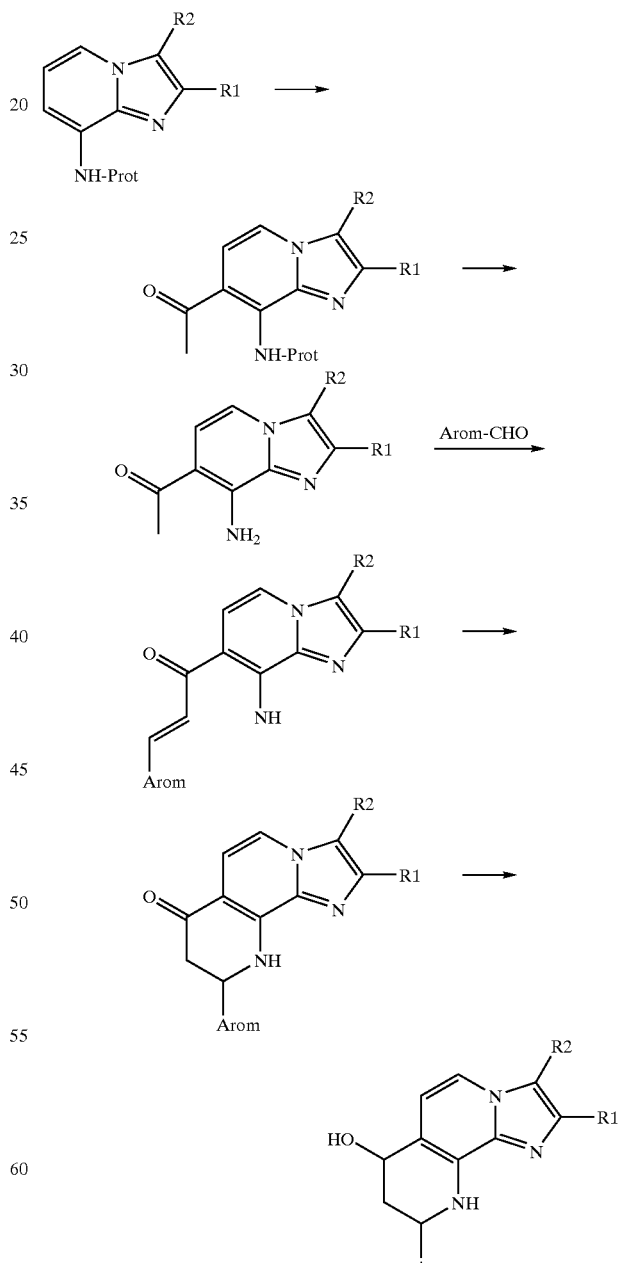

Prot in the above scheme represents any desired protective group, for example a pivaloyl group. The introduction of the acetyl group, the condensation with the aldehyde Arom-CHO, the ring closure and the reduction are carried out in a manner known per se. The derivatization, if desired, following this (e.g. conversion of the hydroxy group into an alkoxy group) is likewise carried out in a manner known per se, for example as described by way of example in international patent application WO 00/17200.

Scheme 2:

Preparation of compounds 1 where X=NH, R4a or R4b= hydroxyl, R5a or R5b=hydroxyl and any desired substituents R3a and R3b

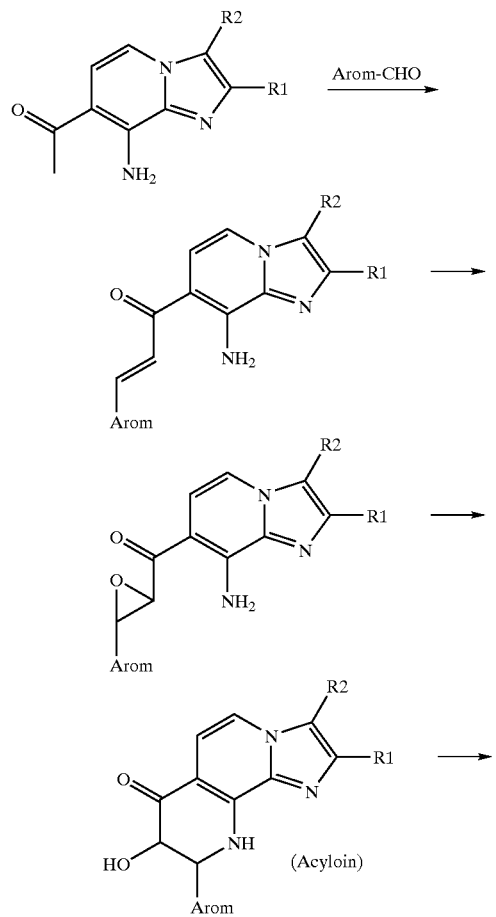

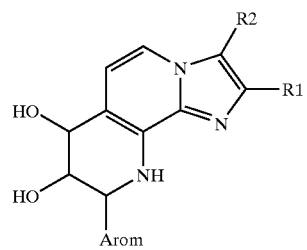

The 7-acetyl-8-aminoimidazopyridine used as a starting material is prepared as outlined in scheme 1. The additional epoxidation compared with scheme 1 is likewise carried out in a manner known per se, for example using hydrogen peroxide as an epoxidizing agent. Alternatively to schemes 1 and 2, the compounds where X=NH can also be prepared according to scheme 8 of international patent application WO98/42707, advantageously with protection of the hydroxy group of the phenylisoserine ester, for example using a suitable silyl group, or—if compounds where R5a/R5b=H are desired—using the corresponding propionic acid derivative without a 2-hydroxy group.

While compounds 1 where X=O, R4a or R4b=hydroxyl, R5a/R5b=H and any desired substituents R3a and R3b can be prepared in analogy to scheme 1, compounds where X=O, R4a or R4b=hydroxyl, R5a or R5b=hydroxyl and any desired substituents R3a and R3b are advantageously prepared according to reaction scheme 3 below.

Scheme 3:

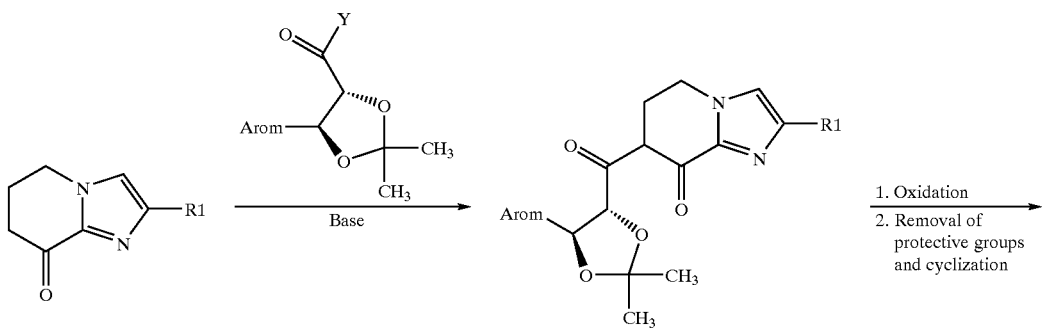

-continued

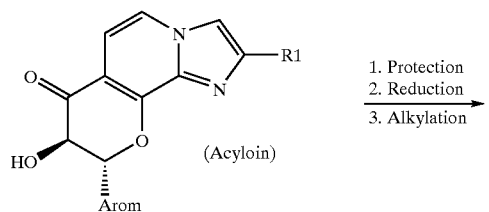
(Acyloin)

1. Protection
2. Reduction
3. Alkylation

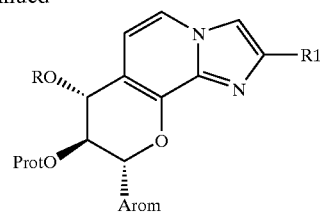

1. Aromatic electrophilic substitution
2. Transformation
3. Removal of protective (Prot) group

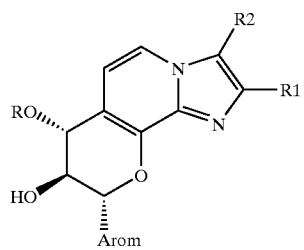

The above scheme 3 shows, by way of example, the enantioselective synthesis of a 7,8-diol (R4a or R4b and R5a or R5b are in each case hydroxyl), which, if desired, can then additionally be alkylated or its hydroxy groups can additionally be derivatized in a suitable manner (e.g. etherified or converted into the groups R41/R51 or R42/R52).

The group Y in scheme 3 is a suitable leaving group, for example a halogen atom, preferably chlorine, or a 1–4C alkoxy group, preferably methoxy. The acylation is carried out in the manner customary to the person skilled in the art, preferably using bis(trimethylsilyl)sodamide or potassamide if the leaving group is a chlorine atom.

The oxidation following the acylation is likewise carried out under conditions which are customary per se, using chloranil, atmospheric oxygen, 2,3-dichloro-5,6-dicyano-p-benzoquinone or manganese dioxide as an oxidant. For the subsequent removal of protective groups and cyclization, certain conditions are to be fulfilled with respect to the auxiliary acid to be used. Formic acid is advantageously employed as an auxiliary acid.

The reduction to the diol is likewise carried out—as already in the case of the reduction according to scheme 2—under standard conditions (see, for example, WO98/54188), sodium borohydride, for example, being employed as a reductant, with the use of which the specified 7,8-trans-diol can be obtained in over 90% diastereomeric purity. The etherification which follows, if desired, and is likewise carried out in a manner customary per se, leads to the compounds of the formula 1* according to the invention in which R4a and R5b are hydrogen.

For the preparation of compounds of the formula 1 in which R5a and R5b are hydrogen, instead of the dioxolane in scheme 3, starting materials to be used are 3-hydroxypropionic acid derivatives (correspondingly protected on the hydroxy group) in which Y (analogously to the above scheme) is a suitable leaving group.

The introduction of the "prodrug" radical R' subsequently to the synthesis for the formation of the substituents R41 or R51 carried out according to schemes 1 to 3 is carried out in the sense of an acylation reaction starting from compounds of the formula 1 in which at least one of the radicals R4a, R4b, 85a and R5b is a hydroxy group, by reaction with compounds of the formula R'—Z in which Z is a suitable leaving group, for example a halogen atom. The reaction is carried out in a manner known per se, preferably in the presence of a suitable auxiliary base. For the preparation of the compounds of the formula 1 in which R4a or R4b is 1–4C-alkoxy or 1–4C-alkoxy-1–4C-alkoxy and R5a or R5b is the radical R5', compounds of the formula 1 in which R4a or R4b is 1–4C-alkoxy or 1–4C-alkoxy-1–4C-alkoxy and R5a or R5b is hydroxyl are reacted with compounds R'—Z. For the preparation of the compounds of the formula 1 in which R4a or R4b is hydroxyl and R5a or R5b is the radical R5', compounds of the formula 1 in which R4a and R4b together are O (oxygen) and R5a or R5b is hydroxyl are reacted with compounds R'—Z. The keto group is then reduced to the hydroxy group. In a similar manner, compounds of the formula 1 are obtained in which the "prodrug" radical is in the 7-position and the hydroxy group or the 1–4C-alkoxy or 1–4C-alkoxy-1–4C-alkoxy radical is in the 8-position.

The alkylation of the compounds obtained according to schemes 1 to 3 to give the compounds of the formula 1 in which R4a, R4b, R5a or R5b has the meaning 1–7C-alkyl, 2–7C-alkenyl, phenyl or phen-1–4C-alkyl can generally be carried out according to schemes 4 and 5 below.

Scheme 4:

Scheme 4 generally outlines the preparation of compounds 1 in which R4a or R4b has the meaning 1–7C-alkyl, 2–7C-alkenyl, phenyl or phen-1–4C-alkyl.

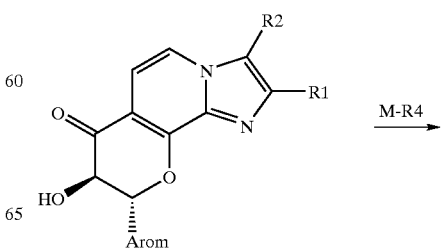

41
-continued

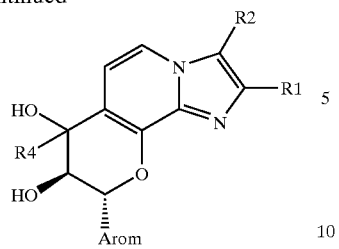

42
-continued

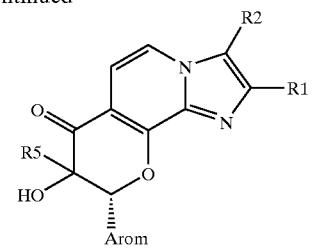

The introduction of the radical R4a or R4b (called R4 for short) in the 7-position is carried out by reaction with a suitable organometallic (M=metal) compound (e.g. methyllithium, phenyllithium, 2,2-dimethylvinylmagnesium bromide etc.) in a manner known per se. The 8-OH group is optionally to be protected, for example using a suitable silyl radical. The alkylated product obtained can then be reacted further, if desired, as described or in a manner known per se (etherification, introduction of a "prodrug" radical etc.).

Schema 5:

Scheme 5 generally outlines the preparation of compounds in which R5a or R5b has the meaning 1–7C-alkyl, 2–7C-alkenyl, phenyl or phen-1–4C-alkyl.

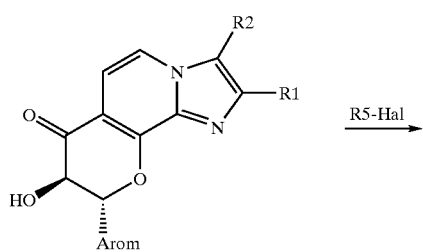

The introduction of the radical R5a or R5b (abbreviated to R5) in the 8-position is carried out, for example, by reaction with a suitable halide (Hal=halogen), such as, for example, methyl iodide, benzyl bromide etc., under suitable, preferably basic conditions in a manner known per se. Advantageously, the reaction can also be carried out under phase-transfer conditions. The alkylated product obtained can then be reacted further, if desired, as described or in a manner known per se (reduction of the 7-oxo group, etherification, introduction of a "prodrug" radical etc.).

With regard to the specific preparation and isolation of the pure enantiomers, reference is made, for example, to the corresponding details in WO00/17200.

The starting compounds shown in schemes 1 to 3 are known (see, for example, EP-A-299470, Kaminski et al., J. Med. Chem. 1985, 28, 876–892, 1989, 32, 1686–1700 and 1991, 34, 533–541 and Angew. Chem. 1996, 108, 589–591) or they can be prepared in a manner analogous to the known compounds, for example according to reaction scheme 6 below.

Scheme 6:

Exemplary preparation of starting compounds needed according to scheme 3 where R1, R2=methyl and various substituents R3b.

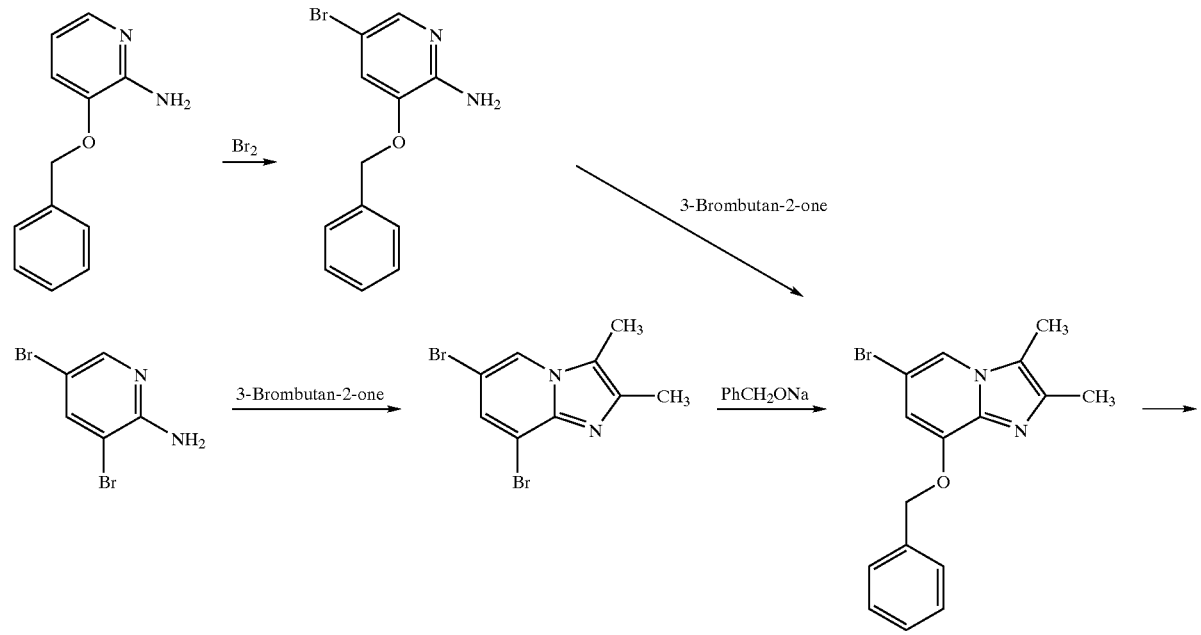

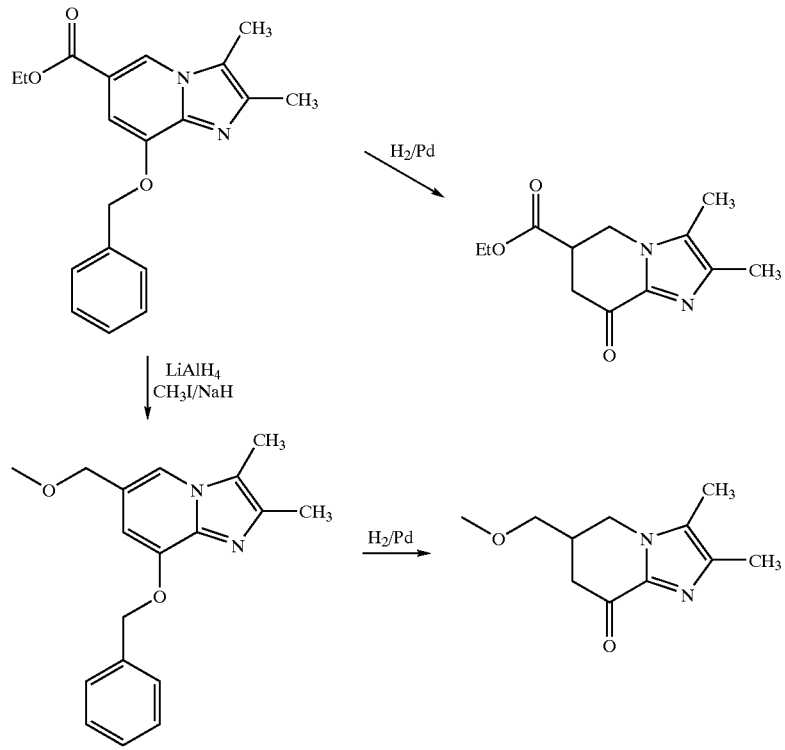

The reactions to give the 8-benzyloxy-6-bromoimidazopyridines are carried out in a manner such as is known to the person skilled in the art. The conversion of the bromine atom into an ethyl ester radical can be carried out in various ways, for example using the Heck reaction (using Pd(II), carbon monoxide and ethanol) or by metallation in the 6-position (using lithium or magnesium) and subsequent Grignard reaction. The metallation also offers the possibility of introducing other desired groups R3b in position 6, for example fluorine, chlorine or the carboxy group. Starting from the ester group, further desired groups R3b can be introduced into position 6, for example hydroxy-1–4C-alkyl radicals (in particular the hydroxymethyl radical), by reduction of the ester radical with lithium aluminum hydride, or 1–4C-alkoxy-1–4C-alkyl radicals (in particular 1–4C-alkoxymethyl radicals) by subsequent etherification as outlined in scheme 6.

The debenzylation/reduction is likewise carried out in a manner known per se, for example using hydrogen/Pd(0). If compounds where R3b=—CO—NR31R32 are desired, an appropriate derivatization can be performed in a manner known per se (conversion of an ester into an amide) at the stage of the 8-benzyloxy-6-ethoxycarbonyl compound or after the debenzylation/reduction, or alternatively also at a later point in time, e.g. at the stage of the acyloin (see schemes 2 and 3).

Starting compounds having various substituents R1 and R2 are known, or they can be prepared—for example based on scheme 6—in a known manner in analogy to known compounds. Alternatively, derivatizations can also be carried out at the stage of the compounds 1. It is thus possible, for example, starting from compounds where R2=H, to prepare compounds where R2=CH$_2$OH (by Vilsmeier reaction and subsequent reduction), where R2=Cl or Br (by chlorination or bromination), where R2=propynyl (from the corresponding bromo compound using the Sonogashira reaction) or where R2=alkoxycarbonyl (from the corresponding bromo compound by Heck carbonylation).

The following examples serve to illustrate the invention in greater detail without restricting it. Likewise, further compounds of the formula 1 whose preparation is not described explicitly can be prepared in an analogous manner or in a manner familiar per se to the person skilled in the art using customary process techniques. The abbreviation min stands for minute(s), h for hour(s) and ee for "enantiomeric excess".

EXAMPLES

Final Products 1. 8-Hydroxy-2,3-dimethyl-9-(3-thienyl)-7,8,9,10-tetrahydroimidazo[1,2-h][1,7]naphthyridin-7-one 1.1 g of 8-amino-7-[2,3-epoxy-1-oxo-3-(3-thienyl)propyl]-2,3-dimethylimidazo[1,2-a]pyridine are dissolved in 20 ml of hexafluoroisopropanol at room temperature, the solvent is stripped off after 19 hours and the residue is purified on silica gel (eluent: methylene chloride/methanol= 100/3). 70 mg of the title compound of m.p. 222–25° C. (diethyl ether) are obtained.

2. 7,8-Dihydroxy-2,3-dimethyl-9-(3-thienyl)-7,8,9,10-tetrahydroimidazo[1,2-h][1,7]naphthyridine 50 mg of 8-hydroxy-2,3-dimethyl-9-(3-thienyl)-7,8,9,10-tetrahydroimidazo[1,2-h][1,7]naphthyridin-7-one are suspended in 5 ml of methanol and treated with 100 mg of sodium borohydride at room temperature with vigorous stirring. After stirring at room temperature for 1 hour, the solvent is stripped off in vacuo, the residue is covered with a layer of 5 ml of water, the mixture is adjusted to pH 1 with a few drops of semisaturated aqueous hydrochloric acid and then adjusted to pH 8 using saturated aqueous sodium hydrogen carbonate solution, extracted three times with 20 ml of methylene chloride each time, the combined organic phases are concentrated to dryness in vacuo and the remaining solid residue is purified on silica gel (eluent: methylene chloride/methanol=13/1). 45 mg of the title compound of m.p. 134–38° C. are obtained.

3. 2,3-Dimethyl-9-(3-thienyl)-7,8,9,10-tetrahydroimidazo[1,2-h][1,7]naphthyridin-7-one 2.6 g of 8-amino-2,3-dimethyl-7-[3-(3-thienyl)-1-oxo-2-propenyl]imidazo[1,2-a]pyridine are treated at room temperature with 20 ml of aqueous 70% strength sulfuric acid, poured onto ice water (100 ml) after 90 minutes, neutralized with aqueous 6 N sodium hydroxide solution and extracted three times with 50 ml of methylene chloride each time. The combined organic phases are washed with water, dried over sodium sulfate, the solvent is stripped off in vacuo and the remaining yellow oil is stirred with 15 ml of diethyl ether. The yellowish solid obtained here is filtered off and dried in vacuo. 1.8 g of the title compound of m.p. 176–77° C. (diethyl ether) are obtained.

4. 7-Hydroxy-2,3-dimethyl-9-(3-thienyl)-7,8,9,10-tetrahydroimidazo[1,2-h][1,7]naphthyridine 1 g of 2,3-dimethyl-9-(3-thienyl)-7,8,9,10-tetrahydroimidazo[1,2-h][1,7]naphthyridin-7-one, suspended in 10 ml of methanol, is treated with 500 mg of sodium borohydride, the solvent is stripped off in vacuo after stirring at room temperature for 1 hour, the yellowish residue is treated with saturated aqueous ammonium chloride solution (100 ml) and the mixture is extracted three times with methylene chloride. The combined organic phases are washed with a little water, dried over sodium sulfate and the solvent is stripped off in vacuo. The remaining solid residue is stirred with a little (15 ml) diethyl ether and then filtered off. 0.88 g of the title compound of m.p. 192–94° C. (diethyl ether) is obtained.

5. 9-(3-Furyl)-8-hydroxy-2,3-dimethyl-7,8,9,10-tetrahydroimidazo[1,2-h][1,7]naphthyridin-7-one Analogously to Example 1, 70 mg of the title compound are obtained by warming 460 mg of 8-amino-7-[2,3-epoxy-1-oxo-3-(3-furyl)propyl]-2,3-dimethyl-7,8,9,10-tetrahydroimidazo[1,2-a]pyridine in hexafluoroisopropanol. $^1$H-NMR (200 MHz, DMSO): δ=2.31 (s, 3H), 2.36 (s, 3H), 4.09–4.15 (m, 1H), 4.62–4.67 (m, 1H), 5.77–5.80 (d, 1 OH), 6.53–6.54 (m, 1H), 6.95–6.98 (d, 1H), 7.44–7.48 (d, 1H), 7.55–7.63 (m, 4H incl.1NH).

6. 9-(3-Furyl)-2,3-dimethyl-7,8,9,10-tetrahydroimidazo[1,2-h][1,7]naphthyridin-7-one Analogously to Example 3, 550 mg of the title compound are obtained by treatment of 1.5 g of 8-amino-2,3-dimethyl-7-[3-(3-furyl)-1-oxo-2-propenyl]imidazo[1,2-a]pyridine with 70% strength sulfuric acid. $^1$H-NMR (200 MHz, DMSO): δ=2.31 (s, 3H), 2.35 (s, 3H), 2.72–3.04 (m, 2H), 4.85–4.92 (m, 1H), 6.54–6.56 (m, 1H), 6.94–6.98 (d, 1H), 7.39–7.43 (d, 1H), 7.50 (s, 1H), 7.55–7.57 (m, 1H), 7.79–7.80 (d, 1NH).

7. 9-(3-Furyl)-7-hydroxy-2,3-dimethyl-7,8,9,10-tetrahydroimidazo[1,2-h][1,7]naphthyridine Analogously to Example 4, 320 mg of the title compound of m.p. 221–22° C. (diethyl ether) are obtained by reaction of 470 mg of 9-(3-furyl)-2,3-dimethyl-7,8,9,10-tetrahydroimidazo[1,2-h][1,7]naphthyridin-7-one with sodium borohydride in methanol.

8. (7R,8R,9R)-8-Hydroxy-7-[2-(2-methoxyethoxy)ethoxy]-2,3-dimethyl-9-phenyl-7,8,9,10-tetrahydroimidazo[1,2-h][1,7]naphthyridine 5 g of (7R,8R,9R)-7,8-dihydroxy-2,3-dimethyl-9-phenyl-7,8,9,10-tetrahydroimidazo[1,2-h][1,7]-naphthyridine are dissolved in 40 ml of 2-(2-methoxyethoxy)ethanol, 3.2 g of sulfuric acid (98% strength) are added and the mixture is warmed at 50° C. for 16 hours. It is then poured onto ice, 100 ml of methylene chloride are added and the mixture is adjusted to pH 7 using aqueous 8 N sodium hydroxide solution. After separation of the organic phase, the aqueous phase is extracted a further two times using 50 ml of methylene chloride each time, the combined organic phases are washed with 100 ml of water, dried over sodium sulfate and the solvent is stripped off in vacuo. The residue is purified on silica gel (eluent: diethyl ether/2-propanol=10/1). 105 mg of the title compound are obtained. $^1$H-NMR (200 MHz, DMSO): δ=2.25 (s, 3H), 2.33 (s, 3H), 3.23 (s, 3H), 3.32–3.47 (m, 6H), 3.59–3.69 (m, 2H), 3.97–4.07 (q, 1H), 4.44–4.47 (m, 2H), 5.18–5.21 (d, 1 OH), 5.85–5.86 (d, 1NH), 6.74–6.78 (d, 1H), 7.19–7.45 (m, 6H).

9. (7S,8R,9R)-8-Hydroxy-7-[2-(2-methoxyethoxy)ethoxy]-2,3-dimethyl-9-phenyl-7,8,9,10-tetrahydroimidazo[1,2-h][1,7]naphthyridine 350 mg of the title compound are obtained by column chromatographic purification on silica gel (eluent: diethyl ether/2-propanol=10/1) of the crude product from the above reaction of (7R,8R,9R)-7,8-dihydroxy-2,3-dimethyl-9-phenyl-7,8,9,10-tetrahydroimidazo[1,2-h][1,7]naphthyridine with 2-(2-methoxyethoxy)ethanol. $^1$H-NMR (200 MHz, DMSO): δ=2.26 (s, 3H), 2.33 (s, 3H), 3.23 (s, 3H), 3.39–4.01 (m, 8H), 3.59–3.69 (m, 2H), 4.25–4.26 (d, 1H), 4.45–4.50 (m, 1H), 4.64–4.68 (d, 1 OH), 5.94–5.95 (d, 1 NH), 6.76–6.79 (d, 1H), 7.24–7.44 (m, 6H).

10. (8R,9R)-8-Hydroxy-2-methyl-9-phenyl-7,8,9,10-tetrahydroimidazo[1,2-h][1,7]naphthyridin-7-one 30 ml of concentrated hydrochloric acid are added dropwise at room temperature in the course of 20 minutes to 29.8g (73.1 mmol) of (8R,9R)-8-(tert-butyldimethylsilanyloxy)-2-methyl-9-phenyl-7,8,9,10-tetrahydroimidazo[1,2-h][1,7]naphthyridin-7-one, dissolved in 30 ml of methanol. The mixture is stirred for a further 30 minutes at room temperature. The methanol is stripped off and the pH of the remaining solution is adjusted to 10 using 2M sodium hydroxide solution. The mixture is extracted three times with 30 ml of dichloromethane each time, the combined dichloromethane phases are washed once with 30 ml of water and the organic phase is dried over magnesium sulfate. The drying agent is filtered off, the filtrate is concentrated and the residue is brought to crystallization using diethyl ether. The crystallizate is filtered off with suction and dried in vacuo at 50° C. 12.2 g (57% of theory) of the title compound are obtained.

11. (7R,8R,9R)-7,8-Dihydroxy-2-methyl-9-phenyl-7,8,9,10-tetrahydroimidazo[1,2-h][1,7]naphthyridine 6 g (20.5 mmol) of (8R,9R)-8-hydroxy-2-methyl-9-phenyl-7,8,9,10-tetrahydroimidazo[1,2-h][1,7]naphthyridin-7-one are suspended in 30 ml of 2-propanol and 2 ml of 0.3% strength methanolic sodium methoxide solution. 0.4 g (10.2 mmol) of sodium borohydride, dissolved in 5 ml of 0.3% methanolic sodium methoxide solution, is added dropwise at 10° C. in the course of 10 minutes. The reaction mixture (suspension) is stirred overnight at room temperature (a solution forms in the course of this). The reaction solution is added to 90 ml of water and extracted three times with 30 ml of ethyl acetate each time. The combined ethyl acetate phases are washed once with water and concentrated. The residue is chromatographed on silica gel (ethyl acetate/2-propanol 95:5). The product fractions are concentrated and crystallized using diethyl ether. The crystals are filtered off with suction and dried at 50° C. in a high vacuum. 4.3 g (71% of theory) of the title compound of m.p. 119° C. (decomposition) are obtained.

12. (7S,8R,9R)- and (7R,8R,9R)-8-Hydroxy-2-methyl-7-(2-methoxyethoxy)-9-phenyl-7,8,9,10-tetrahydroimidazo[1,2-h][1,7]naphthyridine 6 g (20.3 mmol) of (7R,8R,9R)-7,8-dihydroxy-2-methyl-9-phenyl-7,8,9,10-tetrahydroimidazo[1,2-h][1,7]-naphthyridine are introduced into 75 ml of ethylene glycol monomethyl ether at 65° C., treated with 4.9 g (50.8 mmol) of methanesulfonic acid and the mixture is stirred at 65° C. for 1.5 h. The reaction solution is concentrated in a rotary evaporator and residue is treated with 50 ml of dichloromethane and 50 ml of water. The aqueous phase is adjusted to pH 8 by means of saturated sodium hydrogencarbonate solution, the organic phase is separated oft and the aqueous phase is extracted twice using 20 ml of dichloromethane each time. The combined dichloromethane phases are concentrated and the residue is separated by chromatography on silica gel (ethyl acetate/2-propanol/conc. ammonia water 98:2:0.1). The individual product fractions are concentrated and the products are dried at 50° C. in a high vacuum. 1.7 g (23% of theory) of (7S,8R,9R)-8-hydroxy-2-methyl-7-(2-methoxyethoxy)-9-phenyl-7,8,9,10-tetrahydroimidazo[1,2-h][1,7]naphthyridine (12a) of m.p. 149–152° C. and 0.9 g (13% of theory) of (7R,8R,9R)-8-hydroxy-2-methyl-7-(2-methoxyethoxy)-9-phenyl-7,8,9,10-tetrahydroimidazo[1,2-h][1,7]-naphthyridine (12b) of m.p. 108–110° C. are obtained.

13. (7R,8R,9R)-3-Bromo-8-hydroxy-7-(2-methoxyethoxy)-2-methyl-9-phenyl-7,8,9,10-tetrahydroimidazo[1,2-h][1,7]naphthyridine A suspension of 3.30 g (5.90 mmol) (7R,8R,9R)-10-acetyl-3-bromo-7-(2-methoxyethoxy)-2-methyl-9-phenyl-8-pivaloyloxy-7,8,9,10-tetrahydroimidazo[1,2-h][1,7]naphthyridine, 1.00 ml (6.00 mmol) aqueous potassium hydroxide (6 N) and 2.00 ml (51.40 mmol) hydrazine hydrate in methanol is stirred at 60° C. for 4 h. The methanol is removed in vacuo and the reaction mixture is diluted with water. Subsequently the mixture is extracted twice with dichloromethane. The combined organic layers are washed with brine, dried over sodium sulphate and evaporated in vacuo. The crude product is purified by column chromatography (toluene/dioxane/acetic acid: 8/1/1) to give 1.50 g (3.47 mmol, 59%) of the title compound as a light yellow solid with a melting point of 153–154° C. (acetone).

14. (7R,8R,9R)-3-Chloro-8-hydroxy-7-(2-methoxyethoxy)-2-methyl-9-phenyl-7,8,9,10-tetrahydroimidazo[1,2-h][1,7]naphthyridine A suspension of 0.27 g (0.53 mmol) (7R,8R,9R)-10-acetyl-3-chloro-7-(2-methoxyethoxy)-2-methyl-9-phenyl-8-pivaloyloxy-7,8,9,10-tetrahydroimidazo[1,2-h][1,7]naphthyridine, 0.10 ml (0.60 mmol) aqueous potassium hydroxide (6 N) and 0.20 ml (5.14 mmol) hydrazine hydrate in methanol is stirred at 60° C. for 4 h. The methanol is removed in vacuo and the reaction mixture is diluted with water. Subsequently the mixture is extracted twice with dichloromethane. The combined organic layers are washed with brine, dried over sodium sulphate and evaporated in vacuo. The crude product is purified by column chromatography (toluene/dioxane/acetic acid: 8/1/1) to provide 0.34 g (0.88 mmol/51%) of the title compound as a colourless solid with a melting point of 123–126° C. (acetone).

15. (7R,8R,9R)-3-Bromo-7-hydroxy-8-(2-methoxyethoxy)-2-methyl-9-phenyl-7,8,9,10-tetrahydroimidazo[1,2-h][1,7]naphthyridine A suspension of 0.30 g (0.54 mmol) of (7R,8R,9R)-10-acetyl-3-bromo-8-(2-methoxyethoxy)-2-methyl-9-phenyl-7-pivaloyloxy-7,8,9,10-tetrahydroimidazo[1,2-h][1,7]naphthyridine, 0.10 ml (0.60 mmol) aqueous potassium hydroxide (6 N) and 0.20 ml (5.14 mmol) hydrazine hydrate in methanol is stirred al 60° C. for 4 h. The methanol is removed in vacuo and the reaction mixture is diluted with water. Subsequently the mixture is extracted twice with dichloromethane. The combined organic layers are washed with brine, dried over sodium sulphate and evaporated in vacuo. The crude product is purified by column chromatography (toluene/dioxane/acetic acid: 8/1/1) to give 0.12 g (0.28 mmol/52%) of the title compound as an amorphous solid. $^1$H-NMR (200 MHz, [D$_6$] DMSO): δ=2.30 (s, 1H), 3.09 (s, 1H), 3.10–3.30 (m, 2H), 3.45–3.70 (m, 2H), 4.48 (d, 1H), 4.68 (d, 1H), 6.96 (d, 1H), 7.20–7.51 (m, 5H), 7.58 (d, 1H).

16. (7R,8R,9R)-3-Chloro-8-hydroxy-7-(2-methoxyethoxy)-2-methyl-9-phenyl-7H-8,9-dihydro-pyrano[2,3-c]imidazo[1,2-a]pyridine A suspension of 0.70 g (1.48 mmol) (7R,8R,9R)-3-chloro-7-(2-methoxyethoxy)-2-methyl-9-phenyl-8-pivaloyloxy-7H-8,9-dihydro-pyrano[2,3-c]imidazo[1,2-a]pyridine and 0.10 g (0.72 mmol) potassium carbonate in methanol is stirred at 25° C. for 18 h. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by column chromatography (ethyl acetate) to give 0.45 g (1.16 mmol/78%) of the title compound as a colourless solid with a melting point of 146° C. (acetone).

17. (7R,8R,9R)-8-Hydroxy-7-(2-methoxyethoxy)-2-methyl-9-phenyl-7H-8,9-dihydro-pyrano[2,3-c]imidazo[1,2-a]pyridine A suspension of 1.00 g (2.28 mmol) of (7R,8R,9R)-7-(2-Methoxyethoxy)-2-methyl-9-phenyl-8-pivaloyloxy-7H-8,9-dihydro-pyrano[2,3-c]imidazo[1,2-a]pyridine and 0.10 g (1.30 mmol) potassium carbonate in methanol is stirred at 25° C. for 18 h. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by column chromatography (ethyl acetate) to give 0.55 g (1.55 mmol/68%) of the title compound as an amorphous solid. $^1$H-NMR (200 MHz,[D$_6$] DMSO): δ=2.26 (s, 3H), 3.28 (s, 3H), 3.48–3.53 (m, 2H), 3.80–3.96 (m, 2H), 3.98–4.18 (m, 1H), 4.63 (d, 1H); 5.04 (d, 1H), 6.79 (d, 1H), 7.32–7.53 (m, 5H), 7.61 (d, 1H), 8.05 (d, 1H).

18. (7R,8R,9R)-7,8-Dihydroxy-2-methyl-9-phenyl-7H-8,9-dihydropyrano[2,3-c]imidazo[1,2-a]pyridine To a suspension of 0.46 g (1.43 mmol) (8R,9R)-8-Formyloxy-2-methyl-9-phenyl-7H-8,9-dihydro-pyran-7-one [2,3-c]imidazo[1,2-a]pyridine in methanol is added 60 mg (1.50 mmol) sodium borohydride and the mixture is stirred at 25° C. for 1 h. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by column chromatography (dichloromethane/methanol: 13/1) to give 0.31 g (1.05 mmol/73%) of the title compound as a colourless solid with a melting point of 252–254° C. (acetone).

19. (7S,8R,9R)-7,8-Dihydroxy-2-methyl-9-phenyl-7,8,9,10-tetrahydroimidazo[1,2-h][1,7]naphthyridine To a of 0° C. cooled and stirred solution of hydrobromic acid is added 1.00 g (3.39 mmol) (7R,8R,9R)-7,8-dihydroxy-2-methyl 9-phenyl-7,8,9,10-tetrahydroimidazo [1,2-h][1,7]naphthyridine. After 0.5 h the reaction is quenched by adding ice and aqueous ammonia solution until the reaction mixture is transferred to pH 9.8. The precipitated solid is separated, washed with water and dried in vacuo at 60° C. to provide the title compound as a amorph solid. $^1$H-NMR (200 MHz,[D$_6$] DMSO): δ=2.30 (s, 3H), 3.84 (m, 1H), 4.34 (t, 1H), 4.48 (dd, 1H), 6.72 (d, 1H), 7.25–7.45 (m, 5H), 7.56 (d, 1H), 7.73 (d, 1H).

20. (7R,8R,9R)-8-Hydroxy-7-methoxy-2-methyl-9-phenyl-7,8,9,10-tetrahydroimidazo[1,2-h][1,7]naphthyridine To a suspension of 0.62 g (2.10 mmol) (7S,8R,9R)-7,8-dihydroxy-2-methyl-9-phenyl-7,8,9,10-tetrahydroimidazo[1,2-h][1,7]naphthyridine in dimethoxypropane is added 0.51 g (26.2 mmol) p-toluenesulphonic acid and acetone (4.0 ml). The mixture is stirred for 6 h at 60° C. and 96 h at 25° C. The reaction is quenched by adding of saturated aqueous sodium hydrogen carbonate solution. Subsequently the mixture is extracted twice with dichloromethane. The combined organic layers are washed with brine, dried over sodium sulphate and evaporated in vacuo. The crude product is purified by column chromatography (dichloromethane/methanol: 100/3) to give 0.12 g (0.34 mmol/16%) of the title compound as an amorphous solid. $^1$H-NMR (200 MHz,[D$_6$] DMSO): δ=2.29 (s, 3H), 3.25 (s, 3H), 4.05 (q, 1H), 4.32 (d, 1H), 4.47 (dd, 1H), 6.61 (d, 1H), 7.19–7.46 (m, 5H), 7.54 (s, 1H), 7.72 (d, 1H).

21. (7S,8R,9R)-8-Hydroxy-7-methoxy-2-methyl-9-phenyl-7,8,9,10-tetrahydroimidazo[1,2-h][1,7]naphthyridine To a suspension of 0.62 g (2.10 mmol) (7S,8R,9R)-7,8-dihydroxy-2-methyl-9-phenyl-7,8,9,10-tetrahydroimidazo[1,2-h][1,7]naphthyridine in dimethoxypropane is added 0.51 g (26.2 mmol) p-toluenesulphonic acid and acetone (4.0 ml). The mixture is stirred for 6 h at 60° C. and 96 h at 25° C. The reaction is quenched by adding of saturated aqueous sodium hydrogen carbonate solution. Subsequently the mixture is extracted twice with dichloromethane. The combined organic layers are washed with brine, dried over sodium sulphate and evaporated in vacuo. The crude product is purified by column chromatography (dichloromethane/methanol: 100/3) to give 0.18 g (0.52 mmol/25%) of the title compound as an amorphous solid. $^1$H-NMR (200 MHz,[D$_6$] DMSO): δ=2.28 (s, 3H), 3.30 (s, 1H), 3.09–4.03 (m, 1H), 4.06 (d, 1H), 4.49 (dd, 1H), 6.67 (d, 1H), 7.22–7.44 (m, 5H), 7.54 (d, 1H), 7.69 (d, 1H).

22. (7R,8R,9R)-3-Hydroxymethyl-8-hydroxy-7-(2-methoxyethoxy)-2-methyl-9-phenyl-7,8,9,10-tetrahydroimidazo[1,2-h][1,7]naphthyridine A suspension of 0.60 g (1.10 mmol) of (7R,8R,9R)-10-acetyl-3-hydroxymethyl-7-(2-methoxyethoxy)-2-methyl-9-phenyl-8-pivaloyloxy-7,8,9,10-tetrahydroimidazo[1,2-h][1,7]naphthyridine and 0.30 g (2.10 mmol) potassium carbonate in aminoethanol is stirred at 90° C. for 2 h. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by column chromatography (dichloromethane/methanol: 13/1) to give 0.20 g (0.52 mmol/47%) of the title compound as a colourless solid with a melting point of 180–183° C. (diethyl ether).

23. (7R,8R,9R)-3-Hydroxymethyl-8-hydroxy-7-(2-hydroxyethoxy)-2-methyl-9-phenyl-7,8,9,10-tetrahydroimidazo[1,2-h][1,7]naphthyridine A suspension of 0.17 g (0.30 mmol) (7R,8R,9R)-10-acetyl-3-hydroxymethyl-7-(2-hydroxyethoxy)-2-methyl-9-phenyl-8-pivaloyloxy-7,8,9,10-tetrahydroimidazo[1,2-h][1,7]naphthyridine and 0.30 g (2.10 mmol) potassium carbonate in aminoethanol is stirred at 90° C. for 2 h. The reaction is quenched by adding the mixture directly of silica gel for purification by column chromatography (dichloromethane/methanol: 13/1/1) to give 0.02 g (0.06 mmol/19%) of the title compound as a armorph solid. $^1$H-NMR (200 MHz,[D$_6$] DMSO): δ=2.29 (s, 1H), 3.30–3.44 (m, 2H), 3.46–3.65 (m, 2H), 4.01 (q, 1H), 4.47 (t, 2H), 4.70 (d, 2H), 6.79 (d, 1H), 7.20–7.43 (m, 5H), 7.63 (d, 1H).

24. (7R,5R,9R)-2,3-Dimethyl-8-hydroxy-7-(2-hydroxyethoxy)-9-phenyl-7,8,9,10-tetrahydroimidazo[1,2-h][1,7]naphthyridine To a suspension of 2.00 g (6.40 mmol) (7R,8R,9R)-7,8-Dihydroxy-2,3-dimethyl-9-phenyl-7,8,9,10-tetrahydroimidazo[1,2-h][1,7]naphthyridine in 2-methoxyethanol (100 ml) is added 1.26 g (12.8 mmol) sulfuric acid and the mixture is stirred for 3 h at 55° C. Subsequently the reaction is poured out into a of 0° C. cooled aqueous solution of sodium hydroxide (2N). The mixture is extracted with dichloromethane two times. The combined organic layer are washed with water four times, dried over sodium sulfate and concentrated in vacuo. The crude product is purified by column chromatography (diethyl ether/2-propanol: 10/1) to give 0.35 g (0.99 mmol/16%) of the title compound as a colourless solid with a melting point of 107–109° C. (diethyl ether).

25. (7R,8R,9R)-3,9-Diphenyl-8-hydroxy-7-(2-methoxyethoxy)-2-methyl-7,8,9,10-tetrahydroimidazo[1,2-h][1,7]naphthyridine A suspension of 1.14 g (2.05 mmol) of (7R,8R,9R)-10-acetyl-3,9-diphenyl-7-(2-methoxyethoxy)-2-methyl-8-pivaloyloxy-7,8,9,10-tetrahydroimidazo[1,2-h][1,7]naphthyridine and 2.28 g (16.5 mmol) potassium carbonate in aminoethanol is stirred at 60° C. for 4 h. The reaction is quenched by adding of saturated aqueous ammonium chloride solution. Subsequently the mixture is extracted twice with ethyl acetate. The combined organic layers are washed with brine, dried over sodium sulphate and evaporated in vacuo. The crude product is purified by column chromatography (diethyl ether/petrol ether: 7/3) to give 0.52 g (1.21 mmol/60%) of the title compound as a colourless solid with a melting point of 190–192° C. (diethyl ether).

26. (8R,9R)-8-Hydroxy-2-methoxymethyl-3-methyl-9-phenyl-7,8,9,10-tetrahydroimidazo[1,2-h][1,7]naphthyridin-7-one 7.1 g of 7-[(2R,3S)-2,3-O-isopropylidene-3-phenylpropan-1-on-1-yl]-2-methoxymethyl-3-methyl-8-pivaloylaminoimidazo[1,2-a]pyridine are added to 95 ml of 70% sulfuric acid with ice cooling. After addition is complete, the ice bath is removed and stirring is continued for 3 d at ambient temperature. The reaction mixture is poured onto 200 g of crushed ice and the pH adjusted to ca. 9 by adding 10% sodium hydroxide solution. The aqueous phase is extracted with dichloromethane, the organic phase washed with water and dried over anhydrous sodium sulfate. The solvent is evaporated in vacuo and the residue left crystallized from aceton/diethylether to give 3.2 g (65%) of a solid (BYK236888, m.p. 168–173° C.).

27. (7R,8R,9R)-7,8-Dihydroxy-2-methoxymethyl-3-methyl-9-phenyl-7,8,9,10-tetrahydroimidazo[1,2-h][1,7]naphthyridine 6.0 g of (8R,9R)-8-hydroxy-2-methoxymethyl-3-methyl-9-phenyl-7,8,9,10-tetrahydro-imidazo[1,2-h][1,7]naphthyridin-7-one are suspended in 40 ml methanol and 0.6 g sodium borohydride are added in small portions over a period of 30 min. After 1 h at ambient temperature the reaction mixture is poured onto of 60 ml icewater and 2 g ammonium chloride. The organic layer is separated and the aqueous phase extracted three times with dichloromethane. The combined organic phases are dried over anhydrous sodium sulfate and the solvent removed in vacuo. The residue is purified by column chromatography on silica gel (eluent: dichloromethane/methanol 100:1). Crystallization from diethyl ether yields 4.7 g (78%) of the title compound as a light brown solid (BYK237362, m.p. 102–104° C.).

28. (7S,8R,9R)- and (7R,8R,9R)-4-Hydroxy-7-(2-methoxyethoxy)-2-methoxymethyl-3-methyl-9-phenyl-7,8,9,10-tetrahydroimidazo[1,2-h]1,7]naphthyridine 2.0 g of (7R,8R,9R)-7,8-dihydroxy-2-methoxymethyl-3-methyl-9-phenyl-7,8,9,10-tetrahydroimidazo[1,2-h][1,7]naphthyridine are dissolved in 50 ml 2-methoxyethanol and 1 ml of methane sulfonic acid is slowly added. The reaction is heated at 55° C. for 3 h and subsequently poured onto 80 ml icewater and 100 ml dichloromethane. The organic layer is separated and the aqueous phase extracted three times with dichloromethane. The combined organic phases are dried over anhydrous sodium sulfate and the solvent removed in vacuo. The two diastereomers are separated by column chromatography on silica gel (eluent: diethyl ether) to afford 850 mg (36%) of (7S,8R,9R)-8-hydroxy-7-(2-methoxyethoxy)-2-methoxymethyl-3-methyl-9-phenyl-7,8,9,10-tetrahydroimidazo[1,2-h][1,7]naphthyridine (28a, m.p. 63–65° C.) and 400 mg (17%) of (7R,8R,9R)-8-hydroxy-7-(2-methoxyethoxy)-2-methoxymethyl-3-methyl-9-phenyl-7,8,9,10-tetrahydroimidazo[1,2-h][1,7]naphthyridine (28b, m.p. 5–53° C.).

29. (7S,8R,9R)- and (7R,8R,9R)-7-Ethoxy-8-hydroxy-2-methoxymethyl-3-methyl-9-phenyl-7,8,9,10-tetrahydroimidazo[1,2-h][1,7]naphthyridine The title compound 7S,8R,9R (29a) of melting point 145–47° C. (diethylether/acetone,), and the title compound 7R,8R,9R (29b) of melting point 188–90° C. (acetone) are prepared analogously to examples 28.

30. (8R,9R)-8-Hydroxy-2-methyl-9-phenyl-7H-8,9-dihydro-pyran-7-one[2,3-c]imidazo[1,2-a]pyridine To a of 0° C. cooled suspension of 2.08 g (6.50 mmol) (8R,9R)-8-formyloxy-2-methyl-9-phenyl-7H-8,9-dihydro-pyran-7-one[2,3-c]imidazo[1,2-a]pyridine in methanol (40 ml) is added 0.20 g (1.44 mmol) potassium carbonate and is stirred for 2 h at this temperature. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by crystallisation from acetone to provide 1.50 g (5.10 mmol/78%) of the title compound as a colourless solid with a melting point of 173–175° C. (acetone).

Intermediates and Starting Compounds

A. 7-Acetyl-2,3-dimethyl-8-pivaloylaminoimidazo[1,2-a]pyridine

A vigorously stirred solution of 65.4 g of 2,3-dimethyl-8-pivaloylaminoimidazo[1,2-a]pyridine in 1.4 l of diethyl ether is treated dropwise at –78° C. under argon protective gas with 500 ml of a commercially available, 1.5 molar solution of t-butyllithium in n-pentane such that the temperature does not rise above –70° C. The mixture is then cooled to –90° C. in the course of 15 min and 54 ml of acetyl chloride are added dropwise to the dark-red suspension. The mixture is then allowed to warm to –40° C. (30 min), treated with 60 ml of methanol, the contents of the flask are poured onto 1 l of ice water and the aqueous phase is extracted three times with 150 ml of methylene chloride each time. The combined organic phases are washed three times with 100 ml of water each time, dried over sodium sulfate and the solvent is stripped off in vacuo. The residue is purified on silica gel (eluent: ethyl acetate/petroleum ether=3/7). 23.2 g of the title compound are obtained.

B. 7-Acetyl-8-amino-2,3-dimethylimidazo[1,2-a]pyridine

A cooled solution of 80.4 g of 7-acetyl-2,3-dimethyl-8-pivaloylaminoimidazo[1,2-a]pyridine in 720 ml of methanol is treated with 496 ml of concentrated sulfuric acid and heated at reflux for 2.5 hours. It is then poured onto 1 l of ice water, 400 ml of methylene chloride are added and the mixture is adjusted to pH 7 with 10 N sodium hydroxide solution with cooling. After phase separation, the aqueous phase is again extracted twice with 300 ml of methylene chloride each time, the organic phases are collectively washed with 1 l of water, dried over sodium sulfate and the solvent is stripped off in vacuo. The solid residue is purified on silica gel (eluent: ethyl acetate). 22.5 g of the title compound of m.p. 195–97° C. (diethyl ether) are obtained.

C. 8-Amino-2,3-dimethyl-7-[3-(3-thienyl)-1-oxo-2-propenyl]imidazo[1,2-a]pyridine A mixture of 5 g of 7-acetyl-8-amino-2,3-dimethylimidazo[1,2-a]pyridine, 2.9 g of thiophene-3-carboxaldehyde, 1.6 g of sodium hydroxide and 100 ml of ethanol is stirred at room temperature for 3 days. It is then concentrated in vacuo to half the volume, poured onto 100 ml of saturated aqueous ammonium chloride solution and extracted three times with 100 ml of methylene chloride each time. The combined organic phases are washed with a little water, the solvent is stripped off in vacuo and the residue is stirred in ethyl ether. After filtering off and drying in vacuo, 4.6 g of the title compound are obtained.

D. Amino-7-[2,3-epoxy-1-oxo-3-(3-thienyl)propyl]-2,3-dimethylimidazo[1,2-a]pyridine A suspension of 2.6 g of 8-amino-2,3-dimethyl-7-[3-(3-thienyl)-1-oxo-2-propenyl]imidazo[1,2-a]pyridine in 80 ml of ethanol is treated successively with 5.2 ml of 6 N aqueous sodium hydroxide solution and 5 ml of 30% strength aqueous hydrogen peroxide solution, stirred at room temperature for 48 hours, poured onto 200 ml of ice water and adjusted to pH 7–8 with semisatd. aqueous hydrochloric acid. The mixture is then extracted three times with 100 ml of dichloromethane each time, the combined organic phases are washed once with saturated sodium thiosulfate solution and once with 100 ml of distilled water, the solvent is stripped off in vacuo and the residue is purified on silica gel (eluent: methylene chloride/methanol=100/3). 1.2 g of the title compound of m.p. 186–89° C. (diethyl ether) are obtained.

E. 8-Amino-2,3-dimethyl-7-[3-(3-furyl)-1-oxo-2-propenyl]imidazo[1,2-a]pyridine 4.6 g of the title compound are obtained by reaction of 5 g of 7-acetyl-8-amino-2,3-dimethylimidazo[1,2-a]pyridine with 2.9 g of furan-3-carbaldehyde analogously to Example C.

F. 8-Amino-7-[2,3-epoxy-1-oxo-3-(3-furyl)propyl]-2,3-dimethyl-7,8,9,10-tetrahydroimidazo-[1,2-a]pyridine Analogously to Example D, 0.7 g of the title compound is obtained by reaction of 2.4 g of 8-amino-2,3-dimethyl-7-[3-(3-furyl)-1-oxo-2-propenyl]imidazo[1,2-a]pyridine with hydrogen peroxide (30% strength aqueous).

G. 2-Methyl-6,7-dihydro-5H-imidazo[1,2-a]pyridine-8-one 60 g (251.8 mmol) of 8-benzyloxy-2-methylimidazo[1,2-a]pyridine (Kaminski et al, J. Med. Chem. 1985, 28, 876–892) are hydrogenated on Pd-carbon in 400 ml of methanol at a hydrogen pressure of 55 bar and 70° C. After completion of the hydrogenation, the catalyst is filtered off and the filtrate is concentrated. The residue (38 g) is taken up in dichloromethane and the solution is treated in portions at room temperature with manganese dioxide (109.5 g). The reaction mixture is stirred at room temperature for 22 h and then filtered through silica gel. The filtrate is concentrated to a residue and the crystallizate is dried in vacuo at 60° C. 25.13 g (66% of theory) of the title compound are obtained.

H. (8R,9R)-8-(tert-Butyldimethylsilanyloxy)-2-methyl-8-phenyl-5,6,7,8,9,10-hexahydroimidazo[1,2-h][1,7] naphthyridin-7-one 19.4 g (128.3 mmol) of 2-methyl-6,7-dihydro-5H-imidazo[1,2-a]pyridine-8-one, 42.07 g (130.2 mmol) of ethyl (2R,3R)-3-amino-2-(t-butyldimethylsilanyloxy)-3-phenylpropionate and 0.65 g of p-toluenesulfonic acid monohydrate are boiled under reflux in a water separator for 1.5 h in 100 ml of absolute toluene. The solution is cooled to room temperature and treated with 100 ml of absolute tetrahydrofuran. 154 ml of 2M LDA (lithium diisopropylamide) solution (THF) are then added dropwise to the reaction solution, which is cooled to −25° C. After the LDA addition, the temperature is allowed to rise to 0° C. and the mixture is stirred further at 0° C. for 1 h. The reaction solution is washed once at room temperature with 200 ml of saturated ammonium chloride solution, once with 50 ml of saturated ammonium chloride solution and once with water. The organic phase is concentrated and chromatographed on silica gel (petroleum ether/ethyl acetate 2:1). The concentrated product fractions are dried in a high vacuum. 50.8 g (97% of theory) of the title compound are obtained.

I. (8R,9R)-8-(tert-Butyldimethylsilanyloxy)-2-methyl-9-phenyl-7,8,9,10-tetrahydroimidazo-[1,2-h][1,7] naphthyridin-7-one 50.7 g (123.8 mmol) of (8R,9R)-8-(tert-butyldimethylsilanyloxy)-2-methyl-9-phenyl-5,6,7,8,9,10-hexahydroimidazo[1,2-h][1,7]naphthyridin-7-one are treated in portions at 5° C.–10° C. with 35.6 g (153.5 mmol) of 2,3-dichloro-5,6-dicyano-p-benzoquinone. After the end of the addition, the reaction mixture is stirred at room temperature for 2 days. The reaction mixture is extracted with 150 ml of sodium hydroxide solution and the sodium hydroxide solution phase separated off is extracted with 150 ml of toluene and the combined toluene phases are washed with 150 ml of water. The organic phase is concentrated and the residue is dried overnight in a high vacuum. The solid crystallised in this way is stirred in diisopropyl ether, filtered off with suction and dried in vacuo at 50° C. 10.1 g (20% of theory) of the title compound are obtained.

J. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated at reflux for 9 days, and the precipitate formed is filtered off and dried in vacuo. It is then suspended in 1 l of water and adjusted to pH 8 using 6 molar aqueous sodium hydroxide solution. The precipitate formed here is filtered off and washed with water. 28 g of the title compound of melting point over 90° C. (sintering) are obtained.

K. 8-Benzyloxy-6-bromo-2,3-dimethylimidazo[1,2-a]pyridine 34.8 ml of benzyl alcohol are added dropwise with ice cooling to a suspension of 13.5 g of sodium hydride (60% strength suspension in paraffin) in 510 ml of dimethylformamide and the mixture is stirred for 1 h until the evolution of gas is complete. 51.2 g of 6,8-dibromo-2,3-dimethylimidazo[1,2-a]pyridine are then introduced in small portions and the mixture is stirred at room temperature for 40 h. It is then poured onto 1 l of ice water, extracted three times with 100 ml of dichloromethane each time, the combined organic extracts are washed with saturated aqueous ammonium chloride solution and twice with water, concentrated to dryness in vacuo and the residue is stirred with a little ethyl acetate. The precipitate obtained here is filtered off and dried in vacuo. 43.2 g of the title compound of melting point 151–3° C. (ethyl acetate) are obtained.

L. 8-Benzyloxy-4-ethoxycarbonyl-2,3-dimethylimidazo [1,2-a]pyridine

A mixture of 4 g of 8-benzyloxy-6-bromo-2,3-dimethylimidazo[1,2-a]pyridine, 0.4 g of palladium(II) acetate, 1.33 g of triphenylphosphine, 10 ml of triethylamine and 50 ml of ethanol is heated in a carbon monoxide atmosphere in an autoclave (5 bar) for 16 h, and the volatile components are stripped off in vacuo and chromatographed on silica gel (eluent: ethyl acetate). 2.4 g of the title compound of melting point 140–1° C. (diethyl ether) are obtained.

M. 6-Ethoxycarbonyl-2,3-dimethyl-5,6,7,8-tetrahydroimidazo[1,2-a]pyridin-8-one 3 g of 8-benzyloxy-6-ethoxycarbonyl-2,3-dimethylimidazo[1,2-a]pyridine, suspended in 50 ml of ethanol, are treated with 0.5 g of 10% strength palladium/activated carbon and hydrogenated under a hydrogen pressure of 50 bar for 20 hours at an oil bath temperature of 75° C. After cooling, the catalyst is filtered off, the filtrate is concentrated to 1/5 of the volume in vacuo and the colourless precipitate formed here is filtered off. The filtrate of the precipitate is concentrated to dryness and chromatographed on silica gel (eluent: methylene chloride/methanol 100/3). 0.32 g of 6-ethoxycarbonyl-8-hydroxy-2,3-dimethyl-5,6,7,8-tetrahydroimidazo[1,2-a]pyridine is obtained. For conversion into the title compound, it is dissolved in chloroform, treated with 1.6 g of manganese dioxide and stirred at room temperature for 20 h. The precipitate is then filtered off, the filtrate is concentrated to dryness in vacuo and the residue obtained is purified on silica gel (eluent: methylene chloride/methanol 13/1). 0.2 g of the title compound of melting point 138–40° C. (diethyl ether) is obtained.

N. 8-Benzyloxy-6-hydroxymethyl-2,3-dimethylimidazo [1,2-a]pyridine

A solution of 1.2 g of 8-benzyloxy-6-ethoxycarbonyl-2,3-dimethylimidazo[1,2-a]pyridine in 20 ml of tetrahydrofuran is treated in small portions with 0.2 g of lithium aluminium hydride at room temperature, stirred for one hour and treated successively with 0.2 ml of water, 0.2 ml of 6 molar sodium hydroxide solution and 0.6 ml of water. It is then extracted twice with methylene chloride (50 ml each time), the combined organic phases are concentrated to dryness in vacuo and the residue is purified on silica gel (eluent: methylene chloride/methanol 13/1). 0.4 g of the title compound of melting point 213–5° C. (acetone) is obtained.

O. 6-Hydroxymethyl-2,3-dimethyl-5,6,7,8-tetrahydroimidazo[1,2-a]pyridin-8-one

Analogously to the process described in Example M, the title compound is obtained starting from 8-benzyloxy-6-hydroxymethyl-2,3-dimethylimidazo[1,2-a]pyridine by debenzylation/hydrogenation with palladium/activated carbon.

P. 2,3-Dimethyl-6,7-dihydro-5H-imidazo[1,2-a]pyridine-8-one a) 500 g (2.35 mol) of 8-amino-2,3-dimethylimidazo[1,2-a]pyridine (see EP-A-299470) and 150 g of palladium on activated carbon (10% Pd), suspended in 5.0 l of 6N hydrochloric acid, are stirred at 50° C. for 24 h under a hydrogen pressure of 10 bar. The catalyst is filtered off and the reaction mixture is concentrated to 2.0 l in vacuo. The solution obtained is extracted with dichloromethane. The aqueous phase is adjusted to pH 4.8–5.0 using concentrated ammonia solution and extracted again with dichloromethane. This procedure is repeated ten times. The combined organic phases are dried over sodium sulfate and concentrated. The crude product is crystallised from isopropanol. 334.1 g of the title compound are obtained in the form of pale brown crystals of melting point 178.5° C. (isopropanol).

The title compound can alternatively be prepared as follows:

b) A mixture of 252 g of 8-benzyloxy-2,3-dimethylimidazo[1,2-a]pyridine, 84 g of sodium hydrogen carbonate, 27 g of palladium/carbon catalyst (10% strength) in 500 ml of methanol is initially hydrogenated with hydrogen (5 bar) in an autoclave at 40° C. (20 h). The temperature is then reduced to 20° C. and the hydrogen pressure to 2 bar and hydrogenation is continued until the slow absorption of hydrogen is complete (about 10 h, TLC checking). The catalyst is then filtered off, the filter cake is washed with 200 ml of methanol, the filtrate is concentrated to dryness in vacuo, stirred with 200 ml of chloroform and the insoluble material is filtered off. The filter cake is washed well with 150 ml of chloroform and the filtrate is concentrated to dryness in vacuo. 142 g of the title compound of melting point 178–9° C. (2-propanol) are obtained.

Q. 2-Methyl-6,7-dihydro-5H-imidazo[1,2-a]pyridin-8-one

Analogously to the process described in Example Pa, the title compound is obtained starting from the compound 8-amino-2-methylimidazo[1,2-a]pyridine described in EP-A-299470.

R. 3-Formyl-2-methyl-6,7-dihydro-5H-imidazo[1,2-a]pyridin-8-one

Analogously to the process described in Example Pa, the title compound is obtained starting from the compound 8-amino-3-formyl-2-methylimidazo[1,2-a]pyridine described in EP-A-299470.

S. 6-Chloro-2-methyl-6,7-dihydro-5H-imidazo[1,2-a]pyridin-8-one

Analogously to the process described in Example M, the title compound is obtained starting from 8-benzyloxy-6-chloro-2-methylimidazo[1,2-a]pyridine (EP-A-299470) by debenzylation/hydrogenation with palladium/activated carbon.

T. 6-Chlor-3-formyl-2-methyl-6,7-dihydro-5H-imidazo[1,2-a]pyridin-8-one

Analogously to the process described in Example M, the title compound is obtained starting from 8-benzyloxy-6-chloro-3-formyl-2-methylimidazo[1,2-a]pyridine (EP-A-299470) by debenzylation/hydrogenation with palladium/activated carbon.

U. 8-Benzyloxy-6-methoxymethyl-2,3-dimethylimidazo[1,2-a]pyridine

A suspension of 1.2 g of 8-benzyloxy-6-hydroxymethyl-2,3-dimethylimidazo[1,2-a]pyridine in 12 ml of dimethylformamide is treated with 0.36 g of 60% strength sodium hydride in paraffin under an inert gas atmosphere, stirred for 30 minutes at room temperature until the evolution of gas is complete, and then treated at room temperature with 0.56 ml of methyl iodide. After a reaction time of one hour, it is poured onto 100 ml of ice water and extracted 3 times with 100 ml of ethyl acetate each time. The organic phases are combined and washed with water. The solvent is stripped off in vacuo and the oily residue is chromatographed on silica gel (eluent: methylene chloride/methanol=100/1). 0.34 g of the title compound of melting point 107° C. (diethyl ether) is obtained.

V. 6-Methoxymethyl-2,3-dimethyl-5,6,7,8-tetrahydroimidazo[1,2-a]pyridin-8-one 19.2 g of 8-benzyloxy-6-methoxymethyl-2,3-dimethylimidazo[1,2-a]pyridine, dissolved in 100 ml of methanol, are treated with 1.9 g of palladium (10% strength on activated carbon, Merck) and hydrogenated with hydrogen at 80° C. using a pressure of 50 bar. After absorption of hydrogen is complete, the catalyst is filtered off, washed with methanol and methylene chloride and the combined filtrate is concentrated to dryness in vacuo. After purification on silica gel (eluent: methylene chloride/methanol=13/1), 7.6 g of the title compound of melting point 103–104° C. are obtained.

W. (7R,8R,9R)-10-Acetyl-3,9-diphenyl-7-(2-methoxyethoxy)-2-methyl-8-pivaloyloxy-7,8,9,10-tetrahydroimidazo[1,2-h][1,7]naphthyridine 2.61 g (4.67 mmol) (7R,8R,9R)-10-acetyl-3-bromo-7-(2-methoxyethoxy)-2-methyl-9-phenyl-8-pivaloyloxy-7,8,9,10-tetrahydroimidazo[1,2-h][1,7]naphthyridine, 0.63 g (5.14 mmol) phenylboronic acid, 0.89 g (15.4 mmol) KF (spray-dried), 0.14 g (0.15 mmol) Pd$_2$(dba)$_3$, 0.07 g (0.36 mmol/10 wt % solution in hexane)P(t-Bu)$_3$ and THF (30 ml) are added to a Schlenk tube under argon. Afterwards the Schlenk tube is evacuated and refilled with argon in a freeze-pump-thaw cycles technique three times. The reaction mixture is stirred under argon for 2 d at 25° C. Subsequently the reaction is diluted by adding of ethyl acetate and then filtrated through silica gel. The concentrated crude product is purified by column chromatography (diethyl ether/petrol ether: 6/4) to give 1.80 g (3.24 mmol/70%) of the title compound as an amorphous colourless solid. $^1$H-NMR (200 MHz,[D$_6$] DMSO): δ=1.20 (s, 9H), 2.20 (s, 3H), 2.43 (s, 3H), 3.30 (s, 3H), 3.40–3.57 (m, 2H), 3.88 (t, 2H), 4.64 (d, 1H), 5.35 (t, 1H), 5.83 (d, 1H), 7.00 (d, 1H), 7.10–7.30 (m, 5H), 7.41–7.68 (m, 5H), 8.24 (d, 1H).

X. (7R,8R,9R)-10-Acetyl-4-bromo-7-(2-methoxyethoxy)-2-methyl-9-phenyl-8-pivaloyloxy-7,8,9,10-tetrahydroimidazo[1,2-h][1,7]naphthyridine To a of 0° C. cooled solution of 2.20 g (4.60 mmol) (7R,8R,9R)-10-acetyl-7-(2-methoxyethoxy)-2-methyl-9-phenyl-8-pivaloyloxy-7,8,9,10-tetrahydroimidazo[1,2-h][1,7]naphthyridine in ethanol (20 ml) is added 0.84 g (4.60 mmol) NBS and the mixture is stirred for 1 h. Afterwards the reaction is quenched by adding of saturated aqueous sodium hydrogen carbonate solution and it is extracted twice with dichloromethane. The combined organic layers are washed with brine, dried over sodium sulphate and evaporated in vacuo. The crude product is purified by crystallisation (cyclohexane) to give 1.60 g (2.86 mmol/62%) of the title compound as a colourless solid with a melting point of 166–167° C. (cyclohexane).

Y. (7R,8R,9R)-10-Acetyl-7-(2-methoxyethoxy)-2-methyl-9-phenyl-8-pivaloyloxy-7,8,9,10-tetrahydroimidazo[1,2-h][1,7]naphthyridine To a of −30° C. cooled solution of 7.40 g (17.6 mmol) (7R,8R,9R)-10-acetyl-7-hydroxy-2-methyl-9-phenyl-8-pivaloyloxy-7,8,9,10-tetrahydroimidazo[1,2-h][1,7]naphthyridine in dichloromethane (25 ml) and N-methylpyrrolidinone (25 ml) is added 4.00 g (19.3 mmol) methoxyethyl triflate and 1.40 g (35.2 mmol) sodium hydride and it is stirred for further 2 h at this temperature. The reaction is quenched by adding of saturated aqueous ammonium chloride solution. Subsequently the mixture is extracted twice with dichloromethane. The combined organic layers are washed with brine, dried over sodium sulphate and evaporated in vacuo. The crude product is purified by column chromatography (ethyl acetate/cyclohexane/triethylamine: 5/4/1) to give 7.50 g (15.63 mmol/89%) of the title compound as a yellow amorphous solid. $^1$H-NMR (200 MHz,[D$_6$] DMSO): δ=1.19 (s, 9H), 2.15 (s, 3H), 2.38 (s, 3H), 3.27 (s, 3H), 3.45–3.57 (m, 2H), 3.83–3.93 (m, 2H), 4.60 (d, 1H), 5.31 (t, 1H), 5.79 (d, 1H), 6.94 (s, 1H), 7,20 (s, 5H), 7.74 (s, 1H), 8.43 (d, 1H).

Z. (7R,8R,9R)-10-Acetyl-3-chloro-7-(2-methoxyethoxy)-2-methyl-9-phenyl-8-pivaloyloxy-7,8,9,10-tetrahydroimidazo[1,2-h][1,7]naphthyridin To a of 0° C. cooled solution of 1.00 g (2.10 mmol) (7R,8R,9R)-10-acetyl-7-(2-methoxyethoxy)-2-methyl-9-phenyl-8-pivaloyloxy-7,8,9,10-tetrahydroimidazo[1,2-h][1,7]naphthyridine in ethanol (20 ml) is added 0.28 g (2.10 mmol) NCS and the mixture is stirred for 2 h. Afterwards the reaction is quenched by adding of saturated aqueous sodium hydrogen carbonate solution and is extracted twice with dichloromethane. The combined organic layers are washed with brine, dried over sodium sulphate and evaporated in vacuo. The crude product is purified by column chromatography (ethyl acetate/cylohexane: 1/1) to provide 0.89 g (1.73 mmol/82%) of the title compound as a colourless solid with a melting point of 167–170° C. (cyclohexane).

AA. (7R,8R,9R)-10-Acetyl-3-bromo-8-(2-methoxyethoxy)-2-methyl-9-phenyl-7-pivaloyloxy-7,8,9,10-tetrahydroimidazo[1,2-h][1,7]naphthyridine To a of 0° C. cooled solution of 0.40 g (0.83 mmol) (7R,8R,9R)-10-acetyl-8-(2-methoxyethoxy)-2-methyl-9-phenyl-7-pivaloyloxy-7,8,9,10-tetrahydroimidazo[1,2-h][1,7]naphthyridine in ethanol (5 ml) is added 0.15 g (0.83 mmol) NBS and the mixture is stirred for 1 h. Afterwards the reaction is quenched by adding of saturated aqueous sodium hydrogen carbonate solution and it is extracted twice with dichloromethane. The combined organic layers are washed with brine, dried over sodium sulphate and evaporated in vacuo. The crude product is purified by column chromatography (ether/triethylamine: 95/5) to provide 0.30 g (0.53 mmol/65%) of the title compound as an amorphous solid. $^1$H-NMR (200 MHz,[D$_6$] DMSO): δ=0.96 (s, 9H), 2.09 (s, 3H), 2.42 (s, 3H), 3.23 (s, 3H), 3.40–3.53 (m, 2H), 3.69–3.98 (m, 2H), 4.23 (t, 1H), 5.75 (d, 1H), 6.02 (s, 1H), 6.80 (d, 1H), 7.16 (s, 5H), 8.18 (d, 1H).

BB. (7R,8R,9R)-10-Acetyl-7-hydroxy-2-methylpivaloyloxy-9-phenyl-7,8,9,10-tetrahydroimidazo[1,2-h][1,7]naphthyridine To a of 0° C. cooled suspension of 5.00 g (11.9 mmol) (7R,8R,9R)-10-acetyl-2-methyl-9-phenyl-8-pivaloyloxy-7,8,9,10-tetrahydroimidazo[1,2-h][1,7]naphthyridin-7-one in 2-pro-panol is added 1.60 g (23.80 mmol) sodium cyanoborohydride, methylorange (0.5 ml/ethanolic solution) and ethanolic hydrochloric acid until the solution colour is lasting red. This mixture is stirred for further 2 h at 0° C. Subsequently the reaction is quenched by adding of saturated aqueous sodium hydrogen carbonate solution and is extracted twice with dichloromethane. The combined organic layers are washed with brine, dried over sodium sulphate and evaporated in vacuo to provide 4.90 g (11.6 mmol/98%) of the title compound as an amorphous solid. $^1$H-NMR (200 MHz,[D$_6$] DMSO): δ=1.21 (s, 9H), 2.11 (s, 3H), 2.37 (s, 1H), 4.72 (t, 1H), 5.04–5.10 (m, 1H), 5.66 (d, 1H), 7.00 (d, 1H), 7.17 (s, 5H), 7.74 (s, 1H), 8.45 (d, 1H).

CC. (8R,9R)-10-Acetyl-2-methyl-9-phenyl-8-pivaloyloxy-7,8,9,10-tetrahydroimidazo[1,2-h][1,7]naphthyridin-7-one To a of 0° C. cooled solution of 7.00 g (18.5 mmol) (8R,9R)-2-methyl-9-phenyl-8-pivaloyloxy-7,8,9,10-tetrahydroimidazo[1,2-h][1,7]naphthyridin-7-one in toluene (70 ml) is added 4.10 ml (55.5 mmol) acetyl chloride and 7.70 ml (55.5 mmol) triethylamine and the reaction mixture is stirred for 1 h at 0° C. Afterwards further 4.10 ml (55.5 mmol) acetyl chloride and 7.70 ml (55.5 mmol) triethylamine are added to the reaction mixture and it is warmed up to 25° C. and stirred at this temperature for 1 h. Subsequently the reaction is quenched by adding of saturated aqueous ammonium chloride solution. This mixture is extracted twice with dichloromethane. The combined organic layers are washed with brine, dried over sodium sulphate and evaporated in vacuo. The crude product is crystallised from diethyl ether to provide 5.4 g (12.7 mmol/70%) of the title compound as a colourless solid with a melting point of 168–169° C. (diethyl ether).

DD. (8R,9R)-2-Methyl-9-phenyl-8-pivaloyloxy-7,8,9,10-tetrahydroimidazo[1,2-h][1,7]naphthyridin-7-one To a of 0° C. cooled solution of 10.5 g (35.8 mmol) (8R,9R)-8-hydroxy-2-methyl-9-phenyl-7,8,9,10-tetrahydroimidazo[1,2-h][1,7]naphthyridin-7-one in dichloromethane (110 ml) is added 5.70 ml (41.2 mmol) triethylamine, 0.22 g (1.80 mmol) dimethylaminopyridine and 5.10 ml (41.2 mmol) pivaloyl chloride dissolved in dichloromethane (10 ml). The reaction is stirred for 2 h at 0° C. and warmed up to 25° C. and stirred for further 24 h. Afterwards 5.70 ml (41.2 mmol) triethylamine, 0.22 9 (1.80 mmol) dimethylaminopyridine and 5.10 ml (41.2 mmol) pivaloyl chloride are added to this mixture and it is stirred for 18 h at 25° C. Subsequently the reaction is quenching by adding of water (100 ml). The organic layer is separated, washed with ammonia solution, washed with water two times, dried over sodium sulphate and evaporated in vacuo. The crude product is crystallised from 2-propanol to provide 12.1 g (32.06 mmol/90%) of the title compound as a colourless solid with a melting point of 145–147° C. (2-propanol).

EE. 2-Methyl-7-[(2R,3S)-2,3-O,O-isopropylidene-3-phenylpropan-1-on-1-yl]-6,7-dihydro-5H-imidazo-8-imidazo[1,2-a]pyridin-8-one To a suspension of 5.00 g (33.3 mmol) 2-methyl-6,7-dihydro-5H-imidazo[1,2-a]pyridin-8-one in THF (100 ml) is added dropwise at 10° C. 35.0 ml (1M in THF/35.0 mmol) NaHDMS and 4.90 ml (35.0 mmol) triethylamine. The reaction mixture is stirred for 1 h. Subsequently the mixture is cooled down to −78° C. and 8.42 g (35.0 mmol) (2R,3S)-2,3-O,O-isopropylidene-3-phenyl-propionyl chloride is added slowly. The reaction is stirred for 2 h between −70 to −60° C. and warmed up to 25° C. and stirred 4 h again. The reaction is quenched by adding of saturated aqueous ammonium chloride. This mixture is extracted twice with ethyl acetate. The combined organic layers are washed with brine, dried over sodium sulphate and evaporated in vacuo. The crude product is filtrated over silica gel. The product fractions are concentrated in vacuo and crystallised from diethyl ether to provide 6.10 g (17.2 mmol/51%) of the title compound as a colourless solid with a melting point of 126° C. (diethyl ether).

FF. 2-Methyl-7-[(2R,3S)-2,3-O,O-isopropylidene-3-phenylpropan-1-on-1-yl]imidazo-8-imidazo[1,2-a]pyridin-8-ol A mixture of 20.5 g (57.8 mmol) 2-methyl-7-[(2R,3S)-2,3-O,O-isopropylidene-3-phenylpropan-1-on-1-yl]-6,7-dihydro-5H-imidazo-8-imidazo[1,2-a]pyridin-8-one and 14.2 g (57.8 mmol) chloranil in dioxane (200 ml) is stirred for 40 h at 50° C. Afterwards the solvent is evaporated in vacuo and the crude mixture is purified by column chromatography (toluene/dioxane/acetic acid: 8/1/1). The product fractions are concentrated in vacuo and crystallised from 2-propanol to give the provided compound as a light yellow solid 4.40 g (12.5 mmol/21%) with a melting point of 229° C. (2-propanol)

GG. (8R,9R)-8-Formyloxy-2-methyl-9-phenyl-7H-8,9-dihydro-pyran-7-one[2,3-c]imidazo[1,2-a]pyridine A suspension of 4.40 g (12.5 mmol) 2-methyl-7-[(2R,3S)-2,3-O,O-isopropylidene-3-phenylpropan-1-on-1-yl]imidazo-8-imidazo[1,2-a]pyridin-8-ol in formic acid (100 ml) is stirred at 50° C. for 17 h. Afterwards the acid is remove in vacuo and the residue is dissolved in dichloromethane. The solution is neutralised with saturated aqueous sodium hydrogen carbonate solution, washed with brine, dried over sodium sulfate and evaporated in vacuo. The crude product is purified by column chromatography (dichloromethane/methanol: 80/1) to give the provided compound as a colourless solid 2.20 g (6.82 mmol/55%) with a melting point of 189–191° C. (acetone).

HH. (8R,9R)-2-Methyl-9-phenyl-8-pivaloyloxy-7H-8,9-dihydro-pyran-7-one[2,3-c]imidazo[1,2-a]pyridine To a of 0° C. cooled solution of 2.00 g (6.80 mmol) (8R,9R)-8-hydroxy-2-methyl-9-phenyl-7H-8,9-dihydro-pyran-7-one[2,3-c]imidazo[1,2-a]pyridine in dichloromethane (20 ml) is added 2.34 g (34.0 mmol) imidazole, 1.27 g (10.2 mmol) dimethylaminopyridine and 2.51 ml (20.4 mmol) pivaloyl chloride dissolved in dichloromethane (10 ml). The reaction is stirred for 2 h at 0° C., warmed up to 25° C. and stirred for further 24 h. Afterwards 2.34 g (34.0 mmol) imidazole, 1.27 g (10.2 mmol) dimethylaminopyridine and 2.51 ml (20.4 mmol) pivaloyl chloride are added to this mixture and it is stirred for 48 h at 25° C. Subsequently the reaction is quenched by adding of water. The organic layer is separated, washed with ammonia solution, washed with water two times, dried over sodium sulphate and evaporated in vacuo. The crude product is purified by column chromatography (ethyl acetate/cyclohexane: 1/1) to give 1.40 g (3.70 mmol/54%) of the title compound as an amorphous solid. $^1$H-NMR (200 MHz,[$D_6$] DMSO): $\delta$=0.97 (s, 9H), 2.33 (s, 3H), 5.94 (d, 1H), 6.08 (s, 1H), 7.05 (s, 1H), 7.47–7.50 (m, 3H), 7.62–7.67 (m, 2H), 7.90 (d, 1H), 8.17 (d, 1H).

II. (7R,8R,9R)-7-Hydroxy-2-methyl-9-phenyl-8-pivaloyloxy-7H-8,9-dihydro-pyrano[2,3-c]imidazo[1,2-a]pyridine To a of 0° C. cooled suspension of 1.90 g (5.00 mmol) (8R,9R)-2-methyl-9phenyl-8-pivaloyloxy7H-8,9-dihydro-pyran-7-one[2,3-c]imidazo[1,2-a]pyridine in 2-propanol is added 0.66 g (10.0 mmol) sodium cyanoborohydride, methylorange (0.5 ml/ethanolic solution) and ethanolic hydrochloric acid until the solution colour is lasting red. This mixture is stirred for further 2 h at 0° C. Subsequently the reaction is quenched by adding of saturated aqueous sodium hydrogen carbonate solution and is extracted twice with dichloromethane. The combined organic layers are washed with brine, dried over sodium sulphate and evaporated in vacuo to provide 1.90 g (4.99 mmol/99%) of the title compound as an amorphous solid. $^1$H-NMR (200 MHz,[$D_6$] DMSO): $\delta$=0.88 (s, 9H), 2.27 (d, 3H), 4.91 (s, 1H), 5.25–5.43 (m, 2H), 7.39–7.50 (m, 5H), 7.66 (s, 1H), 8.12 (d, 1H).

JJ. (7R,8R,9R)-7-(2-Methoxyethoxy)-2-methyl-9-phenyl-8-pivaloyloxy-7H-8,9-dihydro-pyrano[2,3c]imidazo[1,2-a]pyridine To a of –30° C. cooled solution of 1.85 g (4.86 mmol) (7R,8R,9R)-7-hydroxy-2-methyl-9-phenyl-8-pivaloyloxy-7H-8,9-dihydro-pyrano[2,3-c]imidazo[1,2-a]pyridine in THF (35 ml)) is added 1.11 g (5.35 mmol) methoxyethyl triflate and 10.2 ml (10.2 mmol) NaHDMS (1 M in THF) and it is stirred for further 10 min at this temperature. The reaction is quenched by adding of saturated aqueous ammonium chloride solution. Subsequently the mixture is extracted twice with ethyl acetate. The combined organic layers are washed with brine, dried over sodium sulphate and evaporated in vacuo to provide 2.13 g (4.85 mmol/100%) of the crude title compound as an amorphous solid. $^1$H-NMR (200 MHz,[$D_6$] DMSO): $\delta$=0.89 (s, 9H), 2.27 (s, 3H), 3.25 (s, 3H), 3.43–3.47 (m, 2H), 3.57–3.67 (m, 1H), 3.72–3.82 (m, 1H), 4.95 (d, 1H), 5.35 (d, 1H), 5.56 (d, 1H), 6.80 (d, 1H), 7.39–7.50 (m, 5H), 7.66 (s, 1H), 8.12 (d, 1H).

KK. 2-Methoxycarbonyl-3-methyl-8-pivaloylaminoimidazo[1,2-a]pyridine

To a stirred solution of 30 g of 2-amino-3-pivaloylaminopyridine in 300 ml of dry tetrahydrofuran are added dropwise under argon 40 g of 3-bromo-2-oxobutanoic acid methylester. The brown solution is stirred at ambient temperature for 3 d. The resulting suspension is poured onto a mixture of icewater and ethyl acetate and the mixture is neutralised by adding 10 M sodium hydroxide solution. The organic phase is separated and the aqueous layer extracted two times with ethyl acetate. The combined organic phases are washed with water and dried over anhydrous sodium sulfate. The solvent is removed in vacuo and the blue coloured residue purified by column chromatography on silica gel to yield 35 g (78%) of a light brown solid (m.p. 132° C).

LL. 2-Hydroxymethyl-3-methylpivaloylaminoimidazo[1,2-a]pyridine

To a solution of 36.6 g of 2-methoxycarbonyl-3-methyl-8-pivaloylaminoimidazo[1,2-a]pyridine in 400 ml of dry tetrahydrofuran are added 5.5 g of lithium aluminium hydride at ambient temperature over a period of 1 h. The reaction mixture is then carefully hydrolysed with 15 ml water and 16 ml 15% sodium hydroxide solution. The precipitate is removed by filtration and washed thoroughly with tetrahydrofuran. The filtrate is washed with 100 ml saturated ammonium chloride solution and concentrated in vacuo. The residue is dissolved in 400 ml tetrahydrofuran/toluene 1:1 (v/v) and the solvent distilled off at 80° C. The precipitate is filtered off and dried in vacuo to yield 27.2 g (83%) of the title compound (m.p. 186–187° C.).

MM. 2-Chloromethyl-3-methyl-8-pivaloylaminoimidazo[1,2-a]pyridine

To a stirred suspension of 13 g of 2-hydroxymethyl-3-methyl-8-pivaloylaminoimidazo[1,2-a]pyridine in 500 ml of dry dichloromethane is added dropwise a solution of 6.5 g thionyl chloride in 50 ml dry dichloromethane at 0–5° C. to give a clear yellow solution. After 2 h the reaction mixture is hydrolysed by adding 200 ml saturated sodium bicarbonate solution under cooling. The resulting mixture is transferred to a separatory funnel and shaken vigorously. The organic layer is separated, washed with water and dried over anhydrous sodium sulfate. The solvent is removed in vacuo to give 12.7 g (92%) of the title compound (m.p. 168° C.).

NN. 2-Methoxymethyl-3-methyl-8-pivaloylaminoimidazo[1,2-a]pyridine

A solution of 12.8 g 2-chloromethyl-3-methyl-8-pivaloylaminoimidazo[1,2-a]pyridine in 600 ml of dry methanol is refluxed for 5 h. The reaction mixture is concentrated in vacuo to half the volume. After addition of 200 ml of saturated sodium bicarbonate solution, the mixture is extracted with diethyl ether. The organic phase is washed with water and dried over anhydrous sodium sulfate. Removal of the solvent in vacuo yields 12.5 g (99%) of the title compound (m.p. 104° C.).

OO. 7-[(2R,3S)-2,3-O-isopropylidene-3-phenylpropan-1-on-1-yl]-2-methoxymethyl-3-methyl-8-pivaloylaminoimidazo[1,2-a]pyridine 60 ml of tert-butyllithium solution (1.5 M in n-pentane) are added dropwise to 50 ml of anhydrous diethyl ether at −90° C. with exclusion of moisture and under an argon atmosphere. A solution of 11.0 g of 2-methoxymethyl-3-methyl-8-pivaloylaminoimidazo[1,2-a]pyridine in 220 ml of anhydrous diethyl ether is added at such a rate that the temperature remains at −90 to −95° C. After 15 min a solution of 21.7 g of methyl (2R,3S)-2,3-O-isopropylidene-3-phenylpropionate in 20 ml of diethyl ether is added quickly (approx. 1 min). After addition is complete the cooling bath is removed. On reaching an internal temperature of −35° C., 40 ml methanol are added. The mixture is transferred to a separatory funnel and diluted with 700 ml water. After separation of the organic layer the water phase is extracted twice with diethyl ether. The combined organic phases are washed with water, dried over anhydrous sodium sulfate and evaporated in vacuo. The residue is purified on silica gel (eluent: diethyl ether) and the product fraction thus obtained further purified by chromatography on silica gel (eluent: acetonitrile). The residue is coevaporated twice with acetonitrile and dichloromethane and dried in vacuo to yield 8.6 g (45%) of the title compound as a yellow solid (m.p. 50–52° C.).

Commercial Utility

The compounds of the formula 1 and their salts have valuable pharmacological properties which make them commercially utilizable. In particular they exhibit a marked inhibition of gastric secretion and an excellent gastric and intestinal protective action in warm-blooded animals, in particular humans. The compounds according to the invention are distinguished here by a high selectivity of action, an advantageous duration of action, a particularly good enteral activity, the absence of significant side effects and a great therapeutic breadth.

"Gastric and intestinal protection" is understood in this connection as meaning the prevention and treatment of gastrointestinal illnesses, in particular gastrointestinal inflammatory illnesses and lesions (such as, for example, stomach ulcer, duodenal ulcer, gastritis, hyperacidic or medicinally related functional gastropathy), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically tolerable salts are outstandingly suitable for use in human and veterinary medicine, where they are used, in particular, for the treatment and/or prophylaxis of disorders of the stomach and/or intestine.

A further subject of the invention are therefore the compounds according to the invention for use in the treatment and/or prophylaxis of the abovementioned illnesses.

The invention likewise comprises the use of the compounds according to the invention for the production of medicaments which are employed for the treatment and/or prophylaxis of the abovementioned illnesses.

The invention furthermore comprises the use of the compounds according to the invention for the treatment and/or prophylaxis of the abovementioned illnesses.

A further subject of the invention are medicaments which contain one or more compounds of the formula 1 and/or their pharmacologically tolerable salts.

The medicaments are prepared by processes which are known per se and familiar to the person skilled in the art. As medicaments, the pharmacologically active compounds (=active compounds) according to the invention are employed either as such, or preferably in combination with suitable pharmaceutical excipients or vehicles in the form of tablets, coated tablets, capsules, suppositories, patches (e.g. as TTS), emulsions, suspensions or solutions, the active compound content advantageously being between 0.1 and 95% and it being possible by the appropriate choice of the excipients and vehicles to obtain a pharmaceutical administration form exactly suited to the active compound and/or to the desired onset of action and/or to the duration of action (e.g. a delayed-release form or an enteric form).

The person skilled in the art is familiar on the basis of his/her expert knowledge with excipients or vehicles which are suitable for the desired pharmaceutical formulations. In addition to solvents, gel formers, suppository bases, tablet excipients and other active compound carriers, it is possible to use, for example, antioxidants, dispersants, emulsifiers, antifoams, flavor corrigents, preservatives, solubilizers, colorants or in particular permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of a number of, preferably 2 to 4, individual doses to achieve the desired result. In the case of parenteral treatment, similar or (in particular in the case of intravenous administration of the active compounds) as a rule lower doses can be used. Any person skilled in the art can easily fix the optimum dose and manner of administration of the active compounds necessary in each case on the basis of his/her expert knowledge.

If the compounds according to the invention and/or their salts are to be employed for the treatment of the abovementioned illnesses, the pharmaceutical preparations can also contain one or more pharmacologically active constituents of other pharmaceutical groups. Examples which may be mentioned are: tranquillizers (for example from the group consisting of the benzodiazepines, e.g. diazepam), spasmolytics (e.g. bietamiverine or camylofin), anticholinergics (e.g. oxyphencyclimine or phencarbamide), local anesthetics (e.g. tetracaine or procaine), and optionally also enzymes, vitamins or amino acids.

In particular to be emphasized in this connection is the combination of the compounds according to the invention with pharmaceuticals which inhibit acid secretion, such as, for example, H2 blockers (e.g. cimetidine, ranitidine), H+/K+ ATPase inhibitors (e.g. omeprazole, pantoprazole), or further with 'peripheral' anticholinergics (e.g. pirenzepine, telenzepine) and with gastrin antagonists with the aim of increasing the main action in an additive or superadditive sense and/or of eliminating or reducing the side effects, or further the combination with antibacterially active substances (such as, for example, cephalosporins, tetracyclines, penicillins, macrolides, nitroimidazoles or alternatively bismuth salts) for controlling *Helicobacter pylori*. Antibacterially active combination components which may be mentioned are, for example, meziocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-inhibiting Action an the Perfused Rat Stomach

In Table A below, the influence of the compounds according to the invention after intravenous administration is shown on the acid secretion stimulated by pentagastrin of the perfused rat stomach in vivo.

TABLE A

| No. | Dose (μmol/kg) i.d. | Inhibition of acid secretion (%) |
|---|---|---|
| 8 | 3 | 100 |
| 9 | 3 | 100 |
| 11 | 3 | 100 |
| 12a | 3 | 100 |
| 12b | 3 | 100 |
| 13 | 3 | 100 |
| 14 | 3 | 100 |
| 16 | 3 | 100 |
| 17 | 3 | 100 |
| 18 | 3 | 100 |
| 20 | 3 | 100 |
| 21 | 3 | 100 |
| 22 | 3 | 100 |

Methodology

The abdomen of anesthetized rats (CD rats, female, 200–250 g; 1.5 g/kg i.m. urethane) was opened after tracheotomy by means of a median upper abdominal incision and a PVC catheter was fixed transorally in the esophagus and a further catheter via the pylorus such that the ends of the tubing just projected into the gastric lumen. The catheter leading from the pylorus led outwards through a side opening in the right abdominal wall.

After thorough rinsing (about 50–100 ml), warm physiological NaCl solution at 37° C. was continuously passed through the stomach (0.5 ml/min, pH 6.8–6.9; Braun-Unita I). The pH (pH meter 632, glass electrode EA 147; φ=5 mm, Metrohm), and, by titration with a freshly prepared 0.01 N NaOH solution to pH 7 (Dosimat 665 Metrohm), the secreted HCl were determined in the effluent in each case collected at an interval of 15 minutes.

The gastric secretion was stimulated by continuous perfusion of 1 μg/kg (=1.65 ml/h) of i.v. pentagastrin (left femoral vein) about 30 min after the end of the operation (i.e. alter determination of 2 preliminary fractions). The substances to be tested were administered intraduodenally in 2,5 ml/kg of liquid volume 60 min after the start of the pentagastrin continuous infusion.

The body temperature of the animals was kept at a constant 37.8–38° C. by infrared irradiation and heat pads (automatic, stepless control by means of rectal temperature sensors).

What is claimed is:
1. A compound of the formula 1

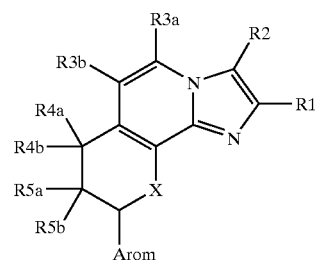

(1)

in which
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, aryl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen, 1–7C-alkyl, 2–7C-alkenyl, phenyl or phen-1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy, 1–4C-alkoxy-1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R41 or the radical R42, or in which R4a and R4b together are O (oxygen) or are 1–7C-alkylidene,
where
R41 is a radical from which a hydroxy group is formed under physiological conditions,
and where
R42 is —O—(CH$_2$)$_m$—S(O)$_n$—R6, —S(O)$_n$—(CH$_2$)$_m$—OH, —S(O)$_n$—(CH$_2$)$_m$—O—R6, —S(O)$_n$—(CH$_2$)$_m$—S(O)$_p$—R6, —O-Alk1 —S(O)$_n$—R6, —S(O)$_n$—R6, —S(O)$_n$-Alk1-OH, —S(O)$_n$-Alk1-O—R6 or —S(O)$_n$-Alk1-S(O)$_p$—R6, in which
R6 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, Alk1 is substituted 2–7C-alkylene or 3–4C-alkenylene by 1–4C-alkyl, hydroxyl, oxo, carboxyl, halogen, amino, 1–4C-alkoxycarbonylamino or phenyl, m is an integer from 2 to 7,
n is the number 0, 1 or 2 and
p is the number 0, 1 or 2, one of the substituents R5a and R5b is hydrogen, 1–7C-alkyl, 2–7C-alkenyl, phenyl or phen-1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy, 1–4C-alkoxy-1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R51 or the radical R52, or in which R5a and R5b together are O (oxygen) or are 1–7C-alkylidene, where
R51 is a radical from which a hydroxy group is formed under physiological conditions,
and where
R52 is —O—(CH$_2$)$_q$—S(O)$_r$—R7, —S(O)$_r$—(CH$_2$)$_q$—OH, —S(O)$_r$—(CH$_2$)$_q$—O—R7, —S(O)$_r$—(CH$_2$)$_q$—S(O)$_t$—R7, —O-Alk2-S(O)$_r$—R7, —S(O)$_r$—R7, —S(O)$_r$-Alk2-OH, —S(O)$_r$-Alk2-O—R7 or —S(O)$_r$-Alk2-S(O)$_t$—R7, in which
R7 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro, Alk2 is 2–7C-alkylene or 3–4C-alkenylene substituted by 1–4C-alkyl, hydroxyl, oxo, carboxyl, halogen, amino, 1–4C-alkoxycarbonylamino or phenyl, q is an integer from 2 to 7,
r is the number 0, 1 or 2 and
t is the number 0, 1 or 2, or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical, which if desired, is wholly or partially halogen-substituted, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where
R8 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl, R9 is hydrogen, 1–4C-alkyl, 1–4C-alkoxy, 1–4C-alkoxycarbonyl, halogen, trifluoromethyl or hydroxyl, R10 is hydrogen, 1–4C-alkyl or halogen and
R11 is hydrogen, 1–4C-alkyl or halogen, where
Aryl is phenyl or substituted phenyl having one, two or three identical or different substituents selected from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano, X is O (oxygen) or NH,
or a hydrate, solvate, salt, hydrate of a salt or solvate of a salt thereof,
where the following are excluded
(a) compounds of the formula 1, in which
R1 is 1–4C-alkyl,
R2 is 1–4C-alkyl or hydroxy-1–4C-alkyl,
R3a is hydrogen or halogen,
R3b is hydrogen or halogen,
one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen),
or in which
one of the substituents R4a and R4b on the one hand and one of the substituents R5a and R5b on the other hand is in each case hydrogen and the other substituents in each case together form a 1–4C-alkylenedioxy radical, Arom is phenyl substituted by R8, R9, R10 and R11, where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is O (oxygen) or NH,
and their salts,
(b) compounds of the formula 1, in which
R1 is 1–4C-alkyl, R2 is 1–4C-alkyl or hydroxy-1–4C-alkyl,
R3a is hydrogen or halogen,
R3b is hydrogen or halogen,
one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen),
where
R42 has the meanings indicated above,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen),
where
R52 has the meanings indicated above,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is NH,
and their salts, (c) compounds of the formula 1, in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen, halogen, fluoro-1–4C-alkyl, 1–4C-alkyl, 2–4C-alkenyl or 2–4C-alkynyl,
R3b is hydrogen, halogen, fluoro-1–4C-alkyl, 1–4C-alkyl, 2–4C-alkenyl or 2–4C-alkynyl,
one of the substituents R4a and R4b is hydrogen and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen),
with the proviso that at least one of the substituents R4a, R4b, R5a and R5b is wholly or mainly halogen-substituted alkoxy,
or in which
one of the substituents R4a and R4b on the one hand and one of the substituents R5a and R5b on the other hand is in each case hydrogen and the other substituents in each case together form a wholly or partially halogen-substituted 1–4C-alkylenedioxy radical,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is NH,
and their salts, (d) compounds of the formula 1, in which
R1 is hydrogen, 1–4C-alkyl, 1–4C-alkoxy-1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen,
R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene,
where
R41 is a radical from which a hydroxy group is formed under physiological conditions,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene,
where
R51 is a radical from which a hydroxy group is formed under physiological conditions,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where one of the substituents R4a and R4b must have the meaning R41 and/or one of the substituents R5a and R5b must have the meaning R51 and/or where at least one of the substituents R4a, R4b, R5a and R5b must have the meaning 1–7C-alkyl, 2–7C-alkenyl, phenyl or phen-1–4C-alkyl and/or where either R4a and R4b or R5a and R5b together must be 1–7C-alkylidene,
Arom is phenyl substituted by R8, R9, R10 and R11,
where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is O (oxygen) or NH,
and their salts, and also (e) compounds of the formula 1, in which
R1 is methyl, R2 is methyl or hydroxymethyl,
R3a is hydrogen,
R3b is halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen and the other is hydroxyl, methoxy, ethoxy, propoxy, isopropoxy, butoxy, methoxyethoxy or methoxypropoxy,
one of the substituents R5a and R5b is hydrogen and the other is hydrogen, hydroxyl, methoxy, ethoxy, propoxy, isopropoxy, butoxy, methoxyethoxy or methoxypropoxy,
Arom is a phenyl radical,
X is O (oxygen) or NH,
and their salts.

2. A compound of the formula 1 as given in claim 1, in which
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
R3a is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen, 1–7C-alkyl, 2–7C-alkenyl, phenyl or phen-1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R41 or the radical R42, or in which R4a and R4b together are O (oxygen) or are 1–7C-alkylidene,
where
R41 is a radical from which a hydroxy group is formed under physiological conditions,
and where
R42 is —O—(CH$_2$)$_m$—S(O)$_n$—R6, —S(O)$_n$—(CH$_2$)$_m$—OH, —S(O)$_n$—(CH$_2$)$_m$—O—R6, —S(O)$_n$—(CH$_2$)$_m$—S(O)$_p$—R6, —O-Alk1-S(O)$_n$—R6, —S(O)$_n$—R6, —S(O)$_n$-Alk1-OH, —S(O)$_n$-Alk1-O—R6 or —S(O)$_n$-Alk1-S(O)$_p$—R6,
in which
R6 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro,
Alk1 is 2–7C-alkylene or 3–4C-alkenylene substituted by 1–4C-alkyl, hydroxyl, oxo, carboxyl, halogen, amino, 1–4C-alkoxycarbonylamino or phenyl,
m is an integer from 2 to 7,
n is the number 0, 1 or 2 and
p is the number 0, 1 or 2,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy, 1–4C-alkylcarbonyloxy, wholly or mainly halogen-substituted 1–4C-alkoxy, the radical R51 or the radical R52, or in which R5a and R5b together are O (oxygen) or are 1–7C-alkylidene,
where
R51 is a radical from which a hydroxy group is formed under physiological conditions,
and where
R52 is —O—(CH$_2$)$_q$—S(O)$_r$—R7, —S(O)$_r$—(CH$_2$)$_q$—OH, —S(O)$_r$—(CH$_2$)$_q$—O—R7, —S(O)$_r$—(CH$_2$)$_q$—S(O)$_r$—R7, —O-Alk2-S(O)$_r$—R7, —S(O)$_r$—R7, —S(O)$_r$-Alk2-OH, —S(O)$_r$-Alk2-O—R7 or —S(O)$_r$-Alk2-S(O)$_r$—R7,
in which
R7 is 1–7C-alkyl, halo-1–4C-alkyl, hydroxy-1–4C-alkyl, 1–4C-alkoxy-1–4C-alkyl, carboxy-1–4C-alkyl, 1–4C-alkoxycarbonyl-1–4C-alkyl or di-1–4C-alkylamino-1–4C-alkyl, Ar or Ar-1–4C-alkyl, where Ar is phenyl or substituted phenyl having one, two or three identical or different substituents selected from the group consisting of 1–4C-alkyl, 1–4C-alkoxy, 1–4C-alkylcarbonyl, 1–4C-alkoxycarbonyl, halogen, trifluoromethyl, difluoromethoxy, trifluoromethoxy, amino, 1–4C-alkoxycarbonylamino, 1–4C-alkoxy-1–4C-alkoxycarbonylamino and nitro,
Alk2 is 2–7C-alkylene or 3–4C-alkenylene substituted by 1–4C-alkyl, hydroxyl, oxo, carboxyl, halogen, amino, 1–4C-alkoxycarbonylamino or phenyl, q is an integer from 2 to 7,
r is the number 0, 1 or 2 and
t is the number 0, 1 or 2,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical which if desired, is wholly or partially halogen-substituted, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl,
where
R8 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl,
R9 is hydrogen, 1–4C-alkyl, 1–4C-alkoxy, 1–4C-alkoxycarbonyl, halogen, trifluoromethyl or hydroxyl,
R10 is hydrogen, 1–4C-alkyl or halogen and
R11 is hydrogen, 1–4C-alkyl or halogen,
where
Aryl is phenyl or substituted phenyl having one, two or three identical or different substituents selected from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano,
X is O (oxygen) or NH,
or a hydrate, solvate, salt, hydrate of a salt or solvate of a salt thereof,
where the following are excluded
(a) compounds of the formula 1, in which
R1 is 1–4C-alkyl,
R2 is 1–4C-alkyl or hydroxy-1–4C-alkyl,
R3a is hydrogen or halogen,
R3b is hydrogen or halogen,
one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen),
or in which
one of the substituents R4a and R4b on the one hand and one of the substituents R5a and R5b on the other hand is in each case hydrogen and the other substituents in each case together form a 1–4C-alkylenedioxy radical,
Arom is phenyl substituted by R8, R9, R10 and R11, where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is O (oxygen) or NH,
and their salts,
(b) compounds of the formula 1, in which
R1 is 1–4C-alkyl,
R2 is 1–4C-alkyl or hydroxy-1–4C-alkyl,
R3a is hydrogen or halogen,
R3b is hydrogen or halogen,
one of the substituents R4a and R4b is hydrogen and the other is hydroxyl, 1–4C-alkoxy, 1–4C-alkoxy-1–4C-alkoxy, 1–4C-alkylcarbonyloxy or the radical R42, or in which R4a and R4b together are O (oxygen),
where
R42 has the meanings indicated above,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R52, or in which R5a and R5b together are O (oxygen),
where
R52 has the meanings indicated above,
or in which
one of the substituents R4a and R4b on the one hand and one of the substituents R5a and R5b on the other hand is in each case hydrogen and the other substituents in each case together form a 1–4C-alkylenedioxy radical,
Arom is phenyl substituted by R8, R9, R10 and R11, where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is NH,
and their salts,
(c) compounds of the formula 1, in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen, halogen, fluoro-1–4C-alkyl, 1–4C-alkyl, 2–4C-alkanyl or 2–4C-alkynyl,
R3b is hydrogen, halogen, fluoro-1–4C-alkyl, 1–4C-alkyl, 2–4C-alkenyl or 2–4C-alkynyl,
one of the substituents R4a and R4b is hydrogen, and the other is hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R4a and R4b together are O(oxygen),
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or wholly or mainly halogen-substituted 1–4C-alkoxy, or in which R5a and R5b together are O (oxygen), with the proviso that at least of the substituents R4a, R4b, R5a and R5b is wholly or mainly halogen-substituted alkoxy, or in which
one of the substituents R4a and R4b on the one hand and one of the substituents R5a and R5b on the other hand is in each case hydrogen and the other substituents in each case together form a wholly or partially halogen-substituted 1–4C-alkylenedioxy radical,
Arom is phenyl substituted by R8, R9, R10 and R11, where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino,
R9 is hydrogen, 1–4C-alkyl, 1–4C-alkoxy or halogen,
R10 is hydrogen and
R11 is hydrogen,
X is NH,
and their salts,
(d) compounds of the formula 1, in which
R1 is hydrogen, 1–4C-alkyl, 1–4C-alkoxy-1–4C-alkyl, or hydroxy-1–4C-alkyl,
R2 is hydrogen, 1–4C-alkyl, hydroxy-1–4C-alkyl, halogen, 2–4C-alkenyl or 2–4C-alkynyl,
R3a is hydrogen,
R3b is hydrogen, halogen, fluoro-1–4C-alkyl, 1–4C-alkyl, 2–4C-alkenyl, 2–4C-alkynyl, carboxyl, —CO-1–4C-alkoxy, hydroxy-1–4C-alkyl, 1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen, 1–7C-alkyl, 2–7C-alkenyl, phenyl or phen-1–4C-alkyl and the other is hydroxyl, 1–4C-alkoxy, 1–4C-alkoxy-1–4C-alkoxy, 1–4C-alkylcarbonyloxy or the radical R41, or in which R4a and R4b together are O (oxygen) or are 1–7C-alkylidene,
where
R41 is a radical from which a hydroxy group is formed under physiological conditions,
one of the substituents R5a and R5b is hydrogen, 1–7C-alkyl, 2–7C-alkenyl, phenyl or phen-1–4C-alkyl and the other is hydrogen, hydroxyl, 1–4C-alkoxy, 1–4C-alkoxy-1–4C-alkoxy, 1–4C-alkylcarbonyloxy or the radical R51, or in which R5a and R5b together are O (oxygen) or are 1–7C-alkylidene,
where
R51 is a radical from which a hydroxy group is formed under physiological conditions,
or in which
one of the substituents R4a and R4b on the one hand and one of the substituents R5a and R5b on the other hand is in each case hydrogen, 1–7C-alkyl, 2–7C-alkenyl, phenyl or phen-1–4C-alkyl, and the other substituents in each case together form a 1–4C-alkylenedioxy radical,
where one of the substituents R4a and R4b must have the meaning R41 and/or one of the substituents R5a and R5b must have the meaning R51 and/or where at least one of the substituents R4a, R4b, R5a and R5b must have the meaning 1–7C-alkyl, 2–7C-alkenyl, phenyl or phen-1–4C-alkyl and/or where either R4a and R4b or R5a and R5b together must be 1–7C-alkylidene,
Arom is phenyl substituted by R8, R9, R10 and R11, where
R8 is hydrogen, 1–4C-alkyl, 1–4C-alkoxy, halogen, trifluoromethyl, 1–4C-alkoxycarbonylamino or 1–4C-alkoxy-1–4C-alkoxycarbonyl amino,
R9 is hydrogen, 1–4C-alkyl, 1–4C-alkoxy or halogen,
R10 is hydrogen and
R11 is hydrogen,
X is O (oxygen) or NH,
and their salts, and also
(e) compounds of the formula 1, in which
R1 is methyl,
R2 is methyl or hydroxymethyl,
R3a is hydrogen,
R3b is halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino, piperidino or morpholino radical,
one of the substituents R4a and R4b is hydrogen and the other is hydroxyl, methoxy, ethoxy, propoxy, isopropoxy, butoxy, methoxyethoxy or methoxypropoxy,
one of the substituents R5a and R5b is hydrogen and the other is hydrogen, hydroxyl, methoxy, ethoxy, propoxy, isopropoxy, butoxy, methoxyethoxy or methoxypropoxy,
Arom is a phenyl radical,
X is O (oxygen) or NH,
and their salts.
3. A compound of the formula 1 as given in claim 1, in which
R1 is hydrogen, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen),
or in which
one of the substituents R4a and R4b on the one hand and one of the substituents R5a and R5b on the other hand is in each case hydrogen and the other substituents in each case together form a 1–4C-alkylenedioxy radical,
and in which R2, R3a, R3b, Arom and X have the meanings given in claim 1, or a hydrate, solvate, salt, hydrate of a salt or solvate of a salt thereof.

4. A compound of the formula 1 as given in claim 1, in which

R2 is hydrogen, aryl, 3–7C-cycloalkyl, 3–7C-cycloalkyl-1–4C-alkyl, 1–4C-alkoxycarbonyl, halogen, 2–4C-alkenyl, 2–4C-alkynyl, fluoro-1–4C-alkyl or cyanomethyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R4a and R5b on the other hand is in each case hydrogen and the other substituents in each case together form a 1–4C-alkylenedioxy radical, and in which R1, R3a, R3b, Arom and X have the meanings given in claim 1, or a hydrate, solvate, salt, hydrate of a salt or solvate of a salt thereof.

5. A compound of the formula 1 as given in claim 1, in which one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R8, R9, R10, R11 and X have the meanings given in claim 1, or a hydrate, solvate, salt, hydrate of a salt or solvate of a salt thereof.

6. A compound of the formula 1 as given in claim 1, in which

R2 is aryl, 3–7C-cycloalkyl, 3–7C-cycloalkyl-1–4C-alkyl, 1–4C-alkoxycarbonyl, fluoro-1–4C-alkyl or cyanomethyl, and in which R1, R3a, R3b, R4a, R4b, R5a, R5b, Arom and X have the meanings given in claim 1, or a hydrate, solvate, salt, hydrate of a salt or solvate of a salt thereof.

7. A compound of the formula 1 as given in claim 1, in which one of the substituents R4a and R4b and/or one of the substituents R5a and R5b have the meaning oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy-1–4C-alkoxy, 3–7C-cycloalkoxy-1–4C-alkoxy or 3–7C-cycloalkyl-1–4C-alkoxy-1–4C-alkoxy, and in which R1, R2, R3a, R3b, Arom and X have the meanings given in claim 1, or a hydrate, solvate, salt, hydrate of a salt or solvate of a salt thereof.

8. A compound of the formula 1 as given in claim 1, in which

Arom is a mono- or bicyclic aromatic radical substituted by R8, R9, R10 and R11, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, with the exception of those compounds in which Arom is phenyl substituted by Ra and Rb with Ra=hydrogen, halogen, 1–4C-alkyl, 1–4C-alkoxy, 1–4C-alkoxycarbonylamino, 1–4C-alkoxy-1–4C-alkoxycarbonylamino or trifluoromethyl and Rb=hydrogen, halogen, 1–4C-alkyl or 1–4C-alkoxy, and in which R1, R2, R3a, R3b, R4a, R4b, R5a, R5b, R8, R9, R10, R11 and X have the meanings given in claim 1, or a hydrate, solvate, salt, hydrate of a salt or solvate of a salt thereof.

9. A compound of the formula 1 as given in claim 1, in which

R2 is hydrogen or fluoro-1–4C-alkyl, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R3a, R3b, Arom and X have the meanings given in claim 1, or a hydrate, solvate, salt, hydrate of a salt or solvate of a salt thereof.

10. A compound of the formula 1 as given in claim 1, in which

R2 is halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C- alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen and the other substituents in each case together form a 1–4C-alkylenedioxy radical, and in which R1, R3a, R3b, Arom and X have the meanings given in claim 1, or a hydrate, solvate, salt, hydrate of a salt or solvate of a salt thereof.

11. A compound of the formula 1 as given in claim 1, in which

R1 is hydrogen, 1–4C-alkyl, 3–7C-cycloalkyl, 1–4C-alkoxy-1–4C-alkyl, 2–4C-alkynyl or fluoro-1–4C-alkyl, R2 is hydrogen, 1–4C-alkyl, aryl, hydroxy-1–4C-alkyl, halogen, 2–4C-alkenyl, 2–4C-alkynyl or fluoro-1–4C-alkyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen or 1–4C-alkyl and the other is hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen or 1–4C-alkyl and the other is hydrogen, hydroxyl, 1–4C-alkoxy, oxo-substituted 1–4C-alkoxy, 3–7C-cycloalkoxy, 3–7C-cycloalkyl-1–4C-alkoxy, hydroxy-1–4C-alkoxy, 1–4C-alkoxy-1–4C-alkoxy or 1–4C-alkoxy-1–4C-alkoxy-1–4C-alkoxy, or in which R5a and R5b together are O (oxygen), Arom is a mono- or bicyclic aromatic radical substituted by R8, R9, R10 and R11, which is selected from the group consisting of phenyl, furanyl (furyl) and thiophenyl (thienyl), where R8 is hydrogen, 1–4C-alkyl, hydroxy-1–4C-alkyl, 1–4C-alkoxy, 1–4C-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl, R9 is hydrogen, 1–4C-alkyl, 1–4C-alkoxy, 1–4C-alkoxycarbonyl, halogen, trifluoromethyl or hydroxyl, R10 is hydrogen and R11 is hydrogen, X is O (oxygen) or NH, or a hydrate, solvate, salt, hydrate of a salt or solvate of a salt thereof, where the following are excluded (a) compounds of the formula 1, in which R1 is 1–4C-alkyl, R2 is 1–4C-alkyl or hydroxy-1–4C-alkyl, R3a is hydrogen, R3b is hydrogen or halogen, one of the substituents R4a and R4b is hydrogen and the other is hydroxyl, 1–4C-alkoxy or 1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, or in which R5a and R5b together are O (oxygen), Arom is phenyl substituted by R8, R9, R10 and R11, where R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino, R9 is hydrogen, 1–4C-alkyl, 1–4C-alkoxy or halogen, R10 is hydrogen and R11 is hydrogen, X is O (oxygen) or NH, and their salts, (b) compounds of the formula 1, in which R1 is hydrogen, 1–4C-alkyl or 1–4C-alkoxy-1–4C-alkyl, R2 is hydrogen, 1–4C-alkyl, hydroxy-1–4C-alkyl, halogen, 2–4C-alkenyl or 2–4C-alkynyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen or 1–4C-alkyl and the other is hydroxyl, 1–4C-alkoxy or 1–4C-alkoxy-1–4C-alkoxy, or in which R4a and R4b together are O (oxygen), one of the substituents R5a and R5b is hydrogen or 1–4C-alkyl and the other is hydrogen, hydroxyl, 1–4C-alkoxy or 1–4C-alkoxy-1–4C-alkoxy, or in which R5a and R5b together are O (oxygen), where at least one of the substituents R4a, R4b, R5a and R5b must have the meaning 1–4C-alkyl, Arom is phenyl substituted by R8, R9, R10 and R11, where R8 is hydrogen, 1–4C-alkyl, 1–4C-alkoxy, halogen, trifluoromethyl, 1–4C-alkoxycarbonylamino or 1–4C-alkoxy-1–4C-alkoxycarbonylamino, R9 is hydrogen, 1–4C-alkyl, 1–4C-alkoxy or halogen, R10 is hydrogen and R11 is hydrogen, X is O (oxygen) or NH, and their salts, and also (c) compounds of the formula 1, in which R1 is methyl, R2 is methyl or hydroxymethyl, R3a is hydrogen, R3b is halogen or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino, piperidino or morpholino radical, one of the substituents R4a and R4b is hydrogen and the other is hydroxyl, methoxy, ethoxy, propoxy, isopropoxy, butoxy, methoxyethoxy or methoxypropoxy, one of the substituents R5a and R5b is hydrogen and the other is hydrogen, hydroxyl, methoxy, ethoxy, propoxy, isopropoxy, butoxy, methoxyethoxy or methoxypropoxy, Arom is a phenyl radical and X is O (oxygen) or NH, and their salts.

12. A compound of the formula 1 as given in claim 1, in which

R1 is 1–4C-alkyl or 1–4C-alkoxy-1–4C-alkyl,

R2 is hydrogen, 1–4C-alkyl, phenyl, hydroxy-1–4C-alkyl or halogen,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, or a hydrate, solvate, salt, hydrate of a salt or solvate of a salt thereof, where the following are excluded compounds of the formula 1, in which R1 is 1–4C-alkyl, R2 is 1–4C-alkyl or hydroxy-1–4C-alkyl, R3a is hydrogen, R3b is hydrogen, one of the substituents R4a and R4b is hydrogen and the other is hydroxyl, 1–4C-alkoxy or 1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, X is O (oxygen) or NH, and their salts.

13. A compound of the formula 1 as given in claim 1, in which

R1 is 1–4C-alkyl or 1–4C-alkoxy-1–4C-alkyl,

R2 is phenyl,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (furyl) or thiophenyl (thienyl), X is O (oxygen) or NH, or a hydrate, solvate, salt, hydrate of a salt or solvate of a salt thereof.

14. A compound of the formula 1 as given in claim 1, in which

R1 is 1–4C-alkyl or 1–4C-alkoxy-1–4C-alkyl,

R2 is hydrogen, 1–4C-alkyl, phenyl, hydroxy-1–4C-alkyl or halogen,

R3a is hydrogen,

R3b is hydrogen, one of the substituents R4a and R4b and/or one of the substituents R5a and R5b have the meaning hydroxy-1–4C-alkoxy or 1–4C-alkoxy-1–4C-alkoxy-1–4C-alkoxy, Arom is phenyl, furanyl (furyl) or thiophenyl (thienyl), X is O (oxygen) or NH, or a hydrate, solvate, salt hydrate of a salt or solvate of a salt thereof.

15. A compound of the formula 1 as given in claim 1, in which

R1 is 1–4C-alkyl or 1–4C-alkoxy-1–4C-alkyl,

R2 is hydrogen, 1–4C-alkyl, phenyl, hydroxy-1–4C-alkyl or halogen,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is furanyl (furyl) or thiophenyl (thienyl), X is O (oxygen) or NH, or a hydrate, solvate, salt, hydrate of a salt or solvate of a salt thereof.

16. A compound of the formula 1 as given in claim 1, in which

R1 is 1–4C-alkyl or 1–4C-alkoxy-1–4C-alkyl,

R2 is hydrogen,

R3a is hydrogen,

R3b is hydrogen, one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy-1–4C-alkoxy, or in which R4a and R4b together are O (oxygen), one of the substituents R5a and R5b is hydrogen and the other is hydrogen, hydroxyl, 1–4C-alkoxy or 1–4C-alkoxy-1–4C-alkoxy, Arom is phenyl, furanyl (fury) or thiophenyl (thienyl), X is O (oxygen) or NH, or a hydrate, solvate, salt, hydrate of a salt or solvate of a salt thereof.

17. A compound of the formula 1 as given in claim 1, in which
R1 is 1–4C-alkyl or 1–4C-alkoxy-1–4C-alkyl,
R2 is halogen,
R3a is hydrogen,
R3b is hydrogen,
one of the substituents R4a and R4b is hydrogen and the other is hydroxyl, 1–4C-alkoxy, hydroxy-1–4-alkoxy, 1–4C-alkoxy-1–4C-alkoxy or 1–4C-alkoxy-1–4C-alkoxy-1–4C-alkoxy, or in which R4a and R4b together are O (oxygen),
one of the substituents R5a and R5b is hydrogen and the other is hydrogen, hydroxyl, 1–4C-alkoxy or 1–4C-alkoxy-1–4C-alkoxy,
Arom is phenyl, furanyl (furyl) or thiophenyl (thienyl),
X is O (oxygen) or NH,
or a hydrate, solvate, salt, hydrate of a salt or solvate of a salt thereof.

18. A compound as claimed in claim 1, identified by the formula 1*,

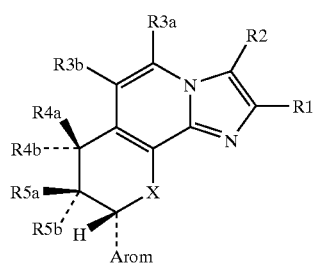

(1*)

in which
R1 is 1–4C-alkyl or 1–4C-alkoxy-1–4C-alkyl,
R2 is hydrogen, 1–4C-alkyl, phenyl, hydroxy-1–4C-alkyl or halogen,
R3a is hydrogen,
R3b is hydrogen,
one of the substituents R4a and R4b is hydrogen and the other is hydroxyl, 1–4C-alkoxy, hydroxy-1–4C-alkoxy, 1–4C-alkoxy-1–4C-alkoxy or 1–4C-alkoxy-1–4C-alkoxy,
R5a is hydrogen, hydroxyl, 1–4C-alkoxy or 1–4C-alkoxy-1–4C-alkoxy,
R5b is hydrogen,
Arom is phenyl, furanyl (furyl) or thiophenyl (thienyl),
X is O (oxygen) or NH,
or a hydrate, solvate, salt, hydrate of a salt or solvate of a salt thereof,
where the following are excluded
compounds of the formula 1, in which
R1 is 1–4C-alkyl,
R2 is 1–4C-alkyl or hydroxy-1–4C-alkyl,
R3a is hydrogen,
R3b is hydrogen,
one of the substituents R4a and R4b is hydrogen and the other is hydroxyl, 1–4C-alkoxy or 1–4C-alkoxy-1–4C-alkoxy, or in which R4a and R4b together are O (oxygen),
one of the substituents R5a and R5b is hydrogen and the other is hydrogen, hydroxyl, 1–4C-alkoxy or 1–4C-alkoxy-1–4C-alkoxy,
Arom is phenyl,
X is O (oxygen) or NH,
and their salts.

19. A compound as claimed in claim 1, identified by the formula 1* as given in claim 18,
in which
R1 is hydrogen, methyl, cyclopropyl, methoxymethyl or trifluoromethyl,
R2 is hydrogen, methyl, chloro, bromo, ethynyl or trifluoromethyl,
R3a is hydrogen,
R3b is hydrogen, fluoro, methyl or the radical —CO—N(CH$_3$)$_2$,
one of the substituents R4a and R4b is hydrogen and the other is hydroxyl, methoxy, ethoxy, propoxy, isopropoxy, butoxy, methoxyethoxy, methoxypropoxy, methoxyethoxyethoxy, 2-oxopropoxy, cyclopropyloxy or cyclopropylmethoxy,
one of the substituents R5a and R5b is hydrogen and the other is hydrogen, hydroxyl, methoxy, ethoxy, propoxy, isopropoxy, butoxy, methoxyethoxy, methoxypropoxy, methoxyethoxyethoxy, 2-oxopropoxy, cyclopropyloxy or cyclopropylmethoxy,
Arom is a phenyl radical and
X is O (oxygen) or NH,
or a hydrate, solvate, salt, hydrate of a salt or solvate of a salt thereof,
where the following are excluded
(a) compounds of the formula 1*, in which
R1 is methyl,
R2 is methyl,
R3a is hydrogen,
R3b is hydrogen,
one of the substituents R4a and R4b is hydrogen and the other is hydroxyl, methoxy, ethoxy, propoxy, isopropoxy, butoxy, methoxyethoxy or methoxypropoxy,
one of the substituents R5a and R5b is hydrogen and the other is hydrogen, hydroxyl, methoxy, ethoxy, propoxy, isopropoxy, butoxy, methoxyethoxy or methoxypropoxy,
Arom is a phenyl radical and
X is O (oxygen) or NH,
and their salts, and
(b) compounds of the formula 1*, in which
R1 is methyl,
R2 is methyl,
R3a is hydrogen,
R3b is fluoro or the radical —CO—N(CH$_3$)$_2$,
one of the substituents R4a and R4b is hydrogen and the other is hydroxyl, methoxy, ethoxy, propoxy, isopropoxy, butoxy, methoxyethoxy or methoxypropoxy,
one of the substituents R5a and R5b is hydrogen and the other is hydrogen, hydroxyl, methoxy, ethoxy, propoxy, isopropoxy, butoxy, methoxyethoxy or methoxypropoxy,
Arom is a phenyl radical and
X is O (oxygen) or NH,
and their salts.

20. A compound as claimed in claim 1, identified by the formula 1* as given in claim 18,
in which
R1 is hydrogen, methyl, cyclopropyl, methoxymethyl or trifluoromethyl,
R2 is hydrogen, methyl, phenyl, hydroxymethyl, chloro, bromo, ethynyl, or trifluoromethyl, R3a is hydrogen,
R3b is hydrogen, fluorine, methyl or the radical —CO—N(CH$_3$)$_2$,
one of the substituents R4a and R4b is hydrogen and the other is hydroxyl, methoxy, ethoxy, propoxy, isopropoxy, butoxy, hydroxyethoxy, methoxyethoxy, methoxypropoxy, methoxyethoxyethoxy, 2-oxopropoxy, cyclopropyloxy or cyclopropylmethoxy,
R5a is hydrogen, hydroxyl, methoxy, ethoxy, propoxy, isopropoxy, butoxy, methoxyethoxy, methoxypropoxy, methoxyethoxyethoxy, 2-oxopropoxy, cyclopropyloxy or cyclopropylmethoxy,
R5b is hydrogen,
Arom is a phenyl radical and
X is O (oxygen) or NH,
or a hydrate, solvate, salt, hydrate of a salt or solvate of a salt thereof,
where the following are excluded
(a) compounds of the formula 1*, in which
R1 is methyl,
R2 is methyl or hydroxymethyl,
R3a is hydrogen,
R3b is hydrogen,
one of the substituents R4a and R4b is hydrogen and the other is hydroxyl, methoxy, ethoxy, propoxy, isopropoxy, butoxy, methoxyethoxy or methoxypropoxy,
R5a is hydrogen, hydroxyl, methoxy, ethoxy, propoxy, isopropoxy, butoxy, methoxyethoxy or methoxypropoxy,
R5b is hydrogen,
Arom is a phenyl radical and
X is O (oxygen) or NH,
and their salts, and
(b) compounds of the formula 1, in which
R1 is methyl,
R2 is methyl or hydroxymethyl,
R3a is hydrogen,
R3b is fluorine or the radical —CO—N(CH$_3$)$_2$,
one of the substituents R4a and R4b is hydrogen and the other is hydroxyl, methoxy, ethoxy, propoxy, isopropoxy, butoxy, methoxyethoxy or methoxypropoxy,
R5a is hydrogen, hydroxyl, methoxy, ethoxy, propoxy, isopropoxy, butoxy, methoxyethoxy or methoxypropoxy,
R5b is hydrogen,
Arom is a phenyl radical and
X is O (oxygen) or NH,
and their salts.

21. A compound as claimed in claim 1, identified by the formula 1* as given in claim 18,
in which
R1 is methyl or methoxymethyl,
R2 is hydrogen, methyl, phenyl, hydroxymethyl, chloro or bromo,
R3a is hydrogen,
R3b is hydrogen,
one of the substituents R4a and R4b is hydrogen and the other is hydroxyl, methoxy, ethoxy, hydroxyethoxy, methoxyethoxy or methoxyethoxyethoxy,
R5a is hydrogen, hydroxyl or methoxyethoxy,
R5b is hydrogen,
Arom is a phenyl radical and
X is O (oxygen) or NH,
or a hydrate, solvate, salt, hydrate of a solvate of a salt thereof,
where the following are excluded
compounds of the formula 1*, in which
R1 is methyl,
R2 is methyl or hydroxymethyl,
R3a is hydrogen,
R3b is hydrogen,
one of the substituents R4a and R4b is hydrogen and the other is hydroxyl, methoxy, ethoxy or methoxyethoxy,
R5a is hydrogen, hydroxyl or methoxyethoxy,
R5b is hydrogen,
Arom is a phenyl radical and
X is O (oxygen) or NH,
and their salts.

22. A compound of the formula 1 as claimed in claim 1, in which
R2 is hydrogen, 3–7C-cycloalkyl, 3–7C-cycloalkyl-1–4C-alkyl, 1–4C-alkoxycarbonyl, halogen, 2–4C-alkenyl, 2–4C-alkynyl, fluoro-1–4C-alkyl or cyanomethyl,
one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen),
or in which
one of the substituents R4a and R4b on the one hand and one of the substituents R5a and R5b on the other hand is in each case hydrogen and the other substituents in each case together form a 1–4C-alkylenedioxy radical,
and in which R1, R3a, R3b, Arom and X have the meanings indicated in claim 1,
or a hydrate, solvate, salt, hydrate of a salt or solvate of a salt thereof.

23. A compound of the formula 1 as claimed in claim 1, in which
R2 is hydrogen or fluoro-1–4C-alkyl,
one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen),
one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen),
or in which
one of the substituents R4a and R4b on the one hand and one of the substituents R5a and R5b on the other hand is in each case hydrogen and the other substituents in each case together form a 1–4C-alkylenedioxy radical,
and in which R1, R3a, R3b, Arom and X have the meanings indicated in claim 1,
or a hydrate, solvate, salt, hydrate of a salt or solvate of a salt thereof.

24. A compound of the formula 1 as claimed in claim 1, in which
R1 is 1–4C-alkyl, R2 is hydrogen, 3–7C-cycloalkyl, 3–7C-cycloalkyl-1–4C-alkyl, 1–4C-alkoxycarbonyl, halogen, 2–4C-alkenyl, 2–4C-alkynyl, fluoro-1–4C-alkyl or cyanomethyl, R3a is hydrogen or halogen, R3b is hydrogen or halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen, and the other substituents in each case together form a methylenedioxy radical (—O—CH$_2$—O—) or an ethylenedioxy radical (—O—CH$_2$—CH$_2$—O—), Arom is phenyl substituted by R8, R9, R10 and R11, where R8 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R9 is hydrogen, halogen, 1–4C-alkyl or 1–4C-alkoxy, R10 is hydrogen and R11 is hydrogen, X is O (oxygen) or NH, or a hydrate, solvate, salt, hydrate of a salt or solvate of a salt thereof.

25. A compound of the formula 1 as claimed in claim 1, in which

R1 is 1–4C-alkyl,

R2 is hydrogen or fluoro-1–4C-alkyl,

R3a is hydrogen or halogen,

R3b is hydrogen or halogen, one of the substituents R4a and R4b is hydrogen and the other is hydroxyl, 1–4C-alkoxy, 1–4C-alkoxy-1–4C-alkoxy or 1–4C-alkylcarbonyloxy, or in which R4a and R4b together are O (oxygen), one of the substituents R5a and R5b is hydrogen and the other is hydrogen, hydroxyl, 1–4C-alkoxy, 1–4C-alkoxy-1–4C-alkoxy or 1–4C-alkylcarbonyloxy, or in which R5a and R5b together are O (oxygen), or in which one of the substituents R4a and R4b on the one hand and one of the substituents R5a and R5b on the other hand is in each case hydrogen, and the other substituents in each case together form a methylenedioxy radical (—O—CH$_2$—O—) or an ethylenedioxy radical (—O—CH$_2$—CH$_2$—O—), Arom is phenyl substituted by R8, R9, R10 and R11, where R8 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl, R9 is hydrogen, halogen, 1–4C-alkyl or 1–4C-alkoxy, R10 is hydrogen and R11 is hydrogen, X is O (oxygen) or NH, or a hydrate, solvate, salt, hydrate of a salt or solvate of a salt thereof.

26. A pharmaceutical composition comprising a compound as claimed in claim 1 and/or a pharmacologically tolerable hydrate, solvate, salt, hydrate of a salt or solvate of a salt thereof together with customary pharmaceutical excipients and/or vehicles.

27. A method of preventing or treating one or more gastrointestinal illnesses in a patient comprising administering to a patient in need thereof a therapeutically effective amount of one or more compounds as claimed in claim 1 or a pharmacologically tolerable hydrate, solvate, salt, hydrate of a salt or solvate of a salt thereof.

* * * * *

UNITED STATES PATENT AND TRADEMARK OFFICE
CERTIFICATE OF CORRECTION

PATENT NO. : 6,869,949 B2
DATED : March 22, 2005
INVENTOR(S) : Senn-Bilfinger et al.

It is certified that error appears in the above-identified patent and that said Letters Patent is hereby corrected as shown below:

Column 72,
Line 52, please delete "2-4C-alkanyl" and replace with -- 2-4C-alkenyl --
Line 59, please delete "O(oxygen)" and replace with -- O (oxygen) --

Column 75,
Line 20, please delete "R4a and R5b" and replace with -- R5a and R5b

Column 80,
Line 25, please delete "salt hydrate" and replace with -- salt, hydrate --
Line 64, please delete "furanyl (fury)" and replace with -- furanyl (furyl) --

Column 81,
Line 9, please delete "hydroxy-1-4-alkoxy" and replace with -- hydroxy-1-4C-alkoxy --

Signed and Sealed this

Twelfth Day of July, 2005

JON W. DUDAS
*Director of the United States Patent and Trademark Office*